United States Patent [19]
Li et al.

[11] Patent Number: 5,880,104
[45] Date of Patent: *Mar. 9, 1999

[54] NUCLEIC ACID RESPIRATORY SYNCYTIAL VIRUS VACCINES

[75] Inventors: Xiaomao Li, Thornhill; Mary E. Ewashysyn; Michel H. Klein, both of Willowdale, all of Canada

[73] Assignee: Connaught Laboratories Limited, North York, Canada

[ * ] Notice: The term of this patent shall not extend beyond the expiration date of Pat. No. 5,843,913.

[21] Appl. No.: 850,041

[22] Filed: May 1, 1997

Related U.S. Application Data

[62] Division of Ser. No. 476,397, Jun. 7, 1995.
[51] Int. Cl.[6] .......................... A61K 31/70; C12N 15/64
[52] U.S. Cl. ............................................. 514/44; 435/914
[58] Field of Search ............................ 424/204.1, 211.1; 435/69.1, 69.3, 91.4, 320.1; 514/44; 536/23.72

[56] References Cited

U.S. PATENT DOCUMENTS 5,589,466  12/1996  Felgner et al. ............................ 514/44

FOREIGN PATENT DOCUMENTS

WO 92/07940  5/1992  WIPO .
WO 93/21310  10/1993  WIPO .

OTHER PUBLICATIONS

Chanock, Robert M. et al, Pediatrics vol. 90 No. 1, Jul. 1992, pp. 137–142.
Prince et al, J. Virol., 61:1851–1854. Jun. 1987.
Crowe et al, PNAS 91:1386–1390. Feb. 1994.
Prince et al, J. Virol. 55:517 Sep. 1985; Virus Res. 3; 193–206. Oct. 1985.
Groothuis et al, N. Engl. J. Med. 329:1524–1530. Nov. 1993.
Walsh et al, J. Infec. Dis., 155: 1198–1204. Jun. 1987.
Paradiso et al, Pediatr. Infect. Dis. J. 13:792–798. Sep. 1994.
Hemming et al, J. Infect. Dis., 152:1083–1087 (1985).
Lounsbah et al, Journal of General Virology 74, 2559–2565 (1993).
Wathan et al. (Feb. 1989) Immunization of cotton rats with the human respiratory syncytial virus F glycoprotein produced using a baculovirus vector. J. Infect. Dis. 159:255–264.
Wertz et al. (Feb. 1987) Expression of the fusion protein of human respiratory syncytial virus from recombinant vaccinia virus vectors and protection of vaccinated mice. J. Virol. 61:293–301.
Tang et al. (May 1993) High–level and erythroid–specific expression of human glucose–6–phosphate dehydrogenase in transgenic mice. J. Biol. Chem. 268:9522–9525.
Collis et al. (1990) Definition of the minimal requirements within the human beta–globin gene and the dominant control region for high level expression. EMBO J. 9:233–240.

Primary Examiner—George C. Elliott
Assistant Examiner—Robert Schwartzman
Attorney, Agent, or Firm—Sim & McBurney

[57] ABSTRACT

Vectors containing a nucleotide sequence coding for an F protein of respiratory syncytial virus (RSV) and a promoter for such sequence, preferably a cytomegalovirus promoter, are described. Such vectors also may contain a further nucleotide sequence located adjacent to the RSV F protein encoding sequence to enhance the immunoprotective ability of the RSV F protein when expressed in vivo. Such vectors may be used to immunize a host, including a human host, by administration thereto. Such vectors also may be used to produce antibodies for detection of RSV infection in a sample.

5 Claims, 27 Drawing Sheets

RESTRICTION MAP OF THE RSV F GENE

AccI EarI PpuMI BclI MamI NlaIV NsiI BspHI

FIG.2A.  NUCLEOTIDE SEQUENCE OF THE RSV F GENE.

```
                                                                        F2-F1CLEAVAGE SITE
ASN THR LYS LYS THR ASN VAL THR LEU SER LYS LYS ARG LYS ARG ARG↓PHE LEU GLY PHE
AATACCAAAAAAACCAATGTAACATTAAGCAAGAAAAGAAAAAGAAAA8AAGATTTCTTGGTTTT
         370            380            390            400            410            420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGGTCCTGCACTTA
         430            440            450            460            470            480

AACAATCCACAACGTTAGGGTCACCGTAACGACATAGATTCCAGGACGTGAAT

GLU GLY VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGGCCGTAGTCAGC
         490            500            510            520            530            540

CTTCCCTCTTCACTTGTTCTAGTTTTCACGAGATGATAGGTGTTGTTCCGGCATCAGTCG

LEU SER ASN GLY VAL SER VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
         550            560            570            580            590            600

AATAGTTTACCTCAATCACAGAATTGGTCGTTCGTTTCACAAGTCTGGAGTTTTATATCTA

LYS GLN LEU LEU PRO ILE VAL ASN LYS GLN SER CYS ARG ILE SER ASN ILE GLU THR VAL
AAACAATTGTTACCTATTGTGAATAAGCAAAGCTGCAGAATATCAAATATAGAAACTGTG
         610            620            630            640            650            660

TTTGTTAACAATGGATAACACTTATTCGTTTCGACGTCTTATAGTTTATATCTTTGACAC

ILE GLU PHE GLN HIS LYS ASN ASN ARG LEU LEU GLU ILE THR ARG GLU PHE SER VAL ASN
ATAGAGTTCCAACAAAAGAACAACAGACTTACATGTTAACTAATAGTGAATTTAGTGTTAAT
         670            680            690            700            710            720

TATCTCAAGGTTGTTTTCTTGTTGTCTGATGATCTCTAATGGTCCCTTAAATCACAATTA

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
         730            740            750            760            770            780

CGTCCACATTGATGTGGACATTCGTGAATGTACAATTGATTATCACTTAATAACAGTAAT
```

FIG.2C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTTCAAATA
TAGTTACTATACGGATATTGTTTACTAGTCTTTTCAATTACAGGTTGTTACAAGTTTAT
            790       800       810       820       830       840

VAL ARG GLN GLN SER TYR SER ILE MET SER ILE ILE LYS GLU VAL LEU ALA TYR VAL
GTTAGACAGCAAAGTTACTCTATCATGTCCATAATAAAAGAGGAAGTCTTAGCATATGTA
CAATCTGTCGTTTCAATGAGATAGTACAGGTATTATTTTCTCCTTCAGAATCGTATACAT
            850       860       870       880       890       900

VAL GLN LEU PRO LEU TYR GLY VAL ILE ASP THR PRO CYS TRP LYS LEU HIS THR SER PRO
GTACAATTACCACTATATGGTGTGATAGATACACCTTGTTGGAAATTACACACATCCCT
CATGTTAATGGTGATATACCACACTATCTATGTGGAACAACCTTTAATGTGTGTAGGGGA
            910       920       930       940       950       960

LEU CYS THR THR ASN THR LYS GLU GLY VAL SER ASN ILE CYS LEU THR ARG THR ASP ARG GLY
CTATGTACAACAACAACAAAAGAAGGTCAAACATCTGTTTAACAAGAACTGACAGAGGA
GATACATGTTGGTTGTGTTTTCTTCCCAGTTGTAGACAAATTGTTCTTGACTGTCTCCT
            970       980       990      1000      1010      1020

TRP TYR CYS ASP ASN ALA GLY SER VAL SER PHE PHE PRO GLN ALA GLU THR CYS LYS VAL
TGGTACTGTGACAATGCAGGATCAGTATCTTTCTTCCCACAAGCTGAAACATGTAAAGTT
ACCATGACACTGTTACGTCCTAGTCATCAGTCATAGAAAGAAGGGTGTTCGACTTTGTACATTCAA
           1030      1040      1050      1060      1070      1080

GLN SER ASN ARG VAL PHE CYS ASP THR MET ASN SER LEU THR LEU PRO SER GLU VAL ASN
CAATCGAATCGAGTGTATTTGTGACACAATGAACAGTTTAACATTACCAAGTGAAGTAAAT
GTTAGCTTAGCTCATAAAACACTGTGTTACTTGTCAAATTGTAATGGTTCACTTCATTTA
           1090      1100      1110      1120      1130      1140

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAAATTATGACTTCAAAAACA
GAGACGTTACAACTGTATAAGTTAGGGTTTATACTAACATTTTAATACTGAAGTTTTTGT
           1150      1160      1170      1180      1190      1200
```

FIG. 2D.

```
ASP VAL SER SER SER VAL ILE THR SER LEU GLY ALA ILE VAL SER CYS TYR GLY LYS THR
GATGTAAGCAGCTCCGTTATCACATCTCTAGGAGCCATTGTGTCATGCTATGGCAAAACT
CTACATTCGTCGAGGCAATAGTGTAGAGATCCTCGGTAACACAGTACGATACCGTTTTGA
         1210                    1230                    1250
                  1220                    1240                    1260

LYS CYS THR ALA SER ASN LYS ASN ARG GLY ILE ILE LYS THR PHE SER ASN GLY CYS ASP
AAATGTACAGCATCCAATAAAATCGTGGAATCATAAAGACATTTCTAACGGGTGTGAT
TTTACATGTCGTAGGTTATTTTAGCACCTTAGTATTTCTGTAAAAGATTGCCCACACTA
         1270                    1290                    1310
                  1280                    1300                    1320

TYR VAL SER ASN LYS GLY [VAL] ASP THR VAL SER VAL GLY ASN THR LEU TYR TYR VAL ASN
TATGTATCAAATAAAGGGGTGGACACTGTGTCTGTAGGTAACACATTATATTATGTAAAT
ATACATAGTTTATTTCCCCACCTGTGACACAGACATCCATTGTGTAATATAACATTTA
         1330                    1350                    1370
                  1340                    1360                    1380

LYS GLN GLU GLY LYS SER LEU TYR VAL LYS GLY GLU PRO ILE ILE ASN PHE TYR ASP PRO
AAGCAAGAAGGCAAAAGTCTCTATGTAAAAGGTGAACCAATAATAAATTTCTATGACCCA
TTCGTTCTTCCGTTTTCAGAGATACATTTTCCACTTGGTTATTATTTAAAGATACTGGGT
         1390                    1410                    1430
                  1400                    1420                    1440

LEU VAL PHE PRO SER ASP GLU PHE ASP ALA SER ILE SER GLN VAL ASN GLU LYS ILE ASN
TTAGTATTTCCCCTCTGATGAATTTGATGCATCAATATCTCAAGTCAATGAGAAGATTAAC
AATCATAAAGGGGAGACTACTTAAACTACGTAGTTATAGAGTTCAGTTACTCTTAATTG
         1450                    1470                    1490
                  1460                    1480                    1500

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAGCATTTAGGCTACTTAATAATGTATTACATTTACGACCATTT
         1510                    1530                    1550
                  1520                    1540                    1560

SER THR THR ASN ILE MET ILE THR THR ILE ILE GLU ILE ILE LEU VAL ILE ILE LEU SER
TCAACCACAAATATCATGATAACTACTATTATAGAGATTATAGTAATTGTTATCA
AGTTGGTGTTTATAGTACTATTGATGATAATATTCTAATATCATTATAACAATAGT
         1570                    1590          ↓TM        1610
                  1580                    1600                    1620
```

```
LEU ILE ALA VAL GLY LEU LEU LEU TYR CYS LYS ALA ARG SER THR PRO VAL THR LEU SER
TTAATTGCTGTTGGACTGCTCCTATACTGTAAGGCCAGAAGCACACCAGTCACACTAAGC
AATTAACGACAACCTGACGAGGATATGACATTCCGGTCTTCGTGTGGTCAGTGTGATTCG
        1630              1640              1650              1660              1670              1680

LYS ASP GLN LEU SER GLY ILE ALA ASN ASN ILE ALA PHE SER ASN
AAGGATCAACTGAGTGGTATAAATATTGCATTTAGTAACTGAATAAAAATAGCACCT
TTCCTAGTTGACTCACCATATTTATAACGTAAATCATTGACTTATTTTATCGTGGA
        1690              1700              1710              1720              1730              1740

AATCATGTTCTTACAATGGTTTACTATATCTGCTCATAGACAACCCATCTATCATTGGATTT
TTAGTACAAGAATGTTACCAAATGATAGACGAGTATCTGTTGGGTAGATAGTAACCTAAA
        1750              1760              1770              1780              1790              1800

TCTTAAAAATCTGAACTTCATCGAAACTCTTATCTATAAACCATCTCACTTACACTATTTA
AGAATTTTAGACTTGAAGTAGCTTTGAGAATAGATATTTGGTAGAGTGAATGTGATAAAT
        1810              1820              1830              1840              1850              1860

AGTAGATTCCTAGTTTATAGTTATAT 3'
TCATCTAAGGATCAAATATCAATATA
        1870              1880
```

NUCLEOTIDE SEQUENCE OF THE RSV F GENE.

```
                              SP
    MET GLU LEU PRO ILE LEU LYS ALA ASN ALA ILE THR THR ILE LEU ALA ALA VAL THR PHE
5'  ATGGAGTTGCCAATCCTCAAAGCAAATGCAATTACCACAATCCTCGCTGCAGTCACATTT
    TACCTCAACGGTTAGGAGTTTCGTTTACGTTAATGGTGTTAGGAGCGACGTCAGTGTAAA
              10        20        30        40        50        60

CYS PHE ALA SER SER GLN ASN ILE THR GLU GLU PHE TYR GLN SER THR CYS SER ALA VAL
    TGCTTTGCTTCTAGTCAAAACATCACTGAAGAATTTTATCAATCAACATGCAGTGCAGTT
    ACGAAACGAAGAGATCAGTTTGTAGTGACTTCTTAAAATAGTTAGTTGTACGTCACGTCAA
              70        80        90       100       110       120

SER LYS GLY TYR LEU SER ALA LEU ARG THR GLY TRP TYR THR SER VAL ILE THR ILE GLU
    AGCAAAGGCTATCTTAGTGCTCTAAGAACTGGTTGGTATACTAGTGTTATAACTATAGAA
    TCGTTTCCGATAGAATCACGAGATTCTTGACCAACCATATGATCACAATATTGATATCTT
             130       140       150       160       170       180

LEU SER ASN ILE LYS GLU ASN LYS CYS ASN GLY THR ASP ALA LYS VAL LYS LEU MET LYS
    TTAAGTAATATCAAGGAAAATAAGTGTAATGGAACAGATGCTAAGGTAAAATTGATGAAA
    AATTCATTATAGTTCCTTTTATTCACATTACCTTGTCTACGATTCCATTTTAACTACTTT
             190       200       210       220       230       240

GLN GLU LEU ASP LYS TYR LYS ASN ALA VAL THR GLU LEU GLN LEU LEU MET GLN SER THR
    CAAGAATTAGATAAATATAAAAATGCTGTAACAGAATTGCAGTTGCTCATGCAAAGCACA
    GTTCTTAATCTATTTATATTTTTACGACATTGTCTTAACGTCAACGAGTACGTTTCGTGT
             250       260       270       280       290       300

PRO ALA ALA ASN ASN ARG ALA ARG ARG GLU LEU PRO ARG PHE MET ASN TYR THR LEU ASN
    CCAGCAGCAAACAATCGAGCCAGAAGAACTACCAAGGTTTATGAATTATACACTCAAC
    GGTCGTCGTTTGTTAGCTCGGTCTTCTTGATGGTTCCAAATACTTAATATGTGAGTTG
             310       320       330       340       350       360
```

FIG.3B.

```
                                                                F2-F1 CLEAVAGE SITE
ASN THR LYS LYS THR ASN VAL THR LEU SER LYS LYS ARG LYS ARG ARG↓PHE LEU GLY PHE
AATACCAAAAAACCAATGTAACATTGTAATTCGTTCTTTCCTTTCTTTCTAAAGAATTCTTGGTTTT
      370        380        390        400        410        420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGGTCCTGCACTTA
      430        440        450        460        470        480

GLU GLY GLU VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGGCCGTAGTCAGC
      490        500        510        520        530        540

LEU SER ASN GLY VAL SER VAL LEU THR SER LYS VAL LEU ASP LEU LYS ASN TYR ILE ASP
CTTCCTCTCACTTGTTCTAGTTTTCACGAGATAGGTGTTTGTTCCGGCATCAGTCG
      550        560        570        580        590        600

LYS GLN HIS LYS ASN ASN ARG LEU LEU GLU ILE THR ARG GLU PHE SER VAL ASN
AAACAATGTTACCTATTGTGAATAAGCAAACTGCAGAATATCAAATATAGAAACTGTG
      610        620        630        640        650        660

ILE GLU PHE GLN HIS LYS ASN ASN ARG LEU LEU GLU ILE THR ARG GLU PHE SER VAL ASN
ATAGAGTTCCAACAAAAGAACAACAGACTACTAGAGATTACCAGGGAATTAGTGTTAAT
      670        680        690        700        710        720

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
      730        740        750        760        770        780
```

FIG.3C.

```
ILE ASN ASP MET PRO ILE THR ASN ASP GLN LYS LYS LEU MET SER ASN ASN VAL GLN ILE
ATCAATGATATGCCTATAACAATGATCAGAAAAAGTTAATGTCCAACAATGTTCAAATA
         790            800            810            820            830            840

VAL ARG GLN GLN SER TYR SER ILE MET SER ILE ILE LYS GLU GLU VAL LEU ALA TYR VAL
TAGTTACTATACGGATATTGTTTACTAGTCTTTTTCAATTACAGGTTGTTACAAGTTTAT
GTTAGACAGCAAAGTTACTCTATCATGTCCATATAAAAGAGGAAGTCTTAGCATATGTA
CAATCTGTCGTTTCAATGAGATAGTACAGGTATTATTTTCTCCTTCAGAATCGTATACAT
         850            860            870            880            890            900

VAL GLN LEU PRO LEU TYR GLY VAL ILE ASP THR PRO CYS TRP LYS LEU HIS THR SER PRO
GTACAATTACCACTATATGGTGTAGATAGATACACCTGTTGGAAATTACACACATCCCT
CATGTTAATGGTGATATACCACTATCTATGTGTGGACAACCTTTAATGTGTAGGGGA
         910            920            930            940            950            960

LEU CYS THR THR ASN THR LYS GLU GLY SER ASN ILE CYS LEU THR ARG THR ASP ARG GLY
CTATGTACAACCAACACAAAGAAGGGTCAAACATCTGTTTAACAAGAACTGACAGAGGA
GATACATGTTGGTTGTTTCTTCCCAGTTGTAGACAAATGTTCTTGACTGTCTCCT
         970            980            990           1000           1010           1020

TRP TYR CYS ASP ASN ALA GLY SER VAL SER PHE PHE PRO GLN ALA GLU THR CYS LYS VAL
TGGTACTGTGACAATGCAGGATCAGTATCTTTCTTCCCACAAGCTGAAACATGTAAAGTT
ACCATGACACACTGTTACGTCCTAGTCATAGAAAGAAGGGTGTTCGACTTTGTACATTCAA
        1030           1040           1050           1060           1070           1080

GLN SER ASN ARG VAL PHE CYS ASP THR MET ASN SER LEU THR LEU PRO SER GLU VAL ASN
CAATCGAATCGAGTATTTGTGACACAATGAACAGTTTAACATTACCAAGTGAAGTAAAT
GTTAGCTTAGCTCACGTCATAAACACTGTGTTACTTGTCAAATTGTAATGGTTCACTTCATTTA
        1090           1100           1110           1120           1130           1140

LEU CYS ASN VAL ASP ILE PHE ASN PRO LYS TYR ASP CYS LYS ILE MET THR SER LYS THR
CTCTGCAATGTTGACATATTCAATCCAAATATGATTGTAAAATTATGACTTCAAAAACA
GAGACGTTACAACTGTATAAGTTAGGTTTATACTAACATTTTAATACTGAAGTTTGT
        1150           1160           1170           1180           1190           1200
```

FIG.3D.

```
ASP VAL SER SER VAL ILE THR SER LEU GLY ALA ILE VAL SER CYS TYR GLY LYS THP
GATGTAAGCAGCTCCGTTATCACATCTCTAGGAGCCATTGTGTCATGCTATGCAAAAGT
     1210           1220           1230           1240           1250      1260
CTACATTCGTCGAGGCAATAGTGTAGAGATCCTCGGTAACACAGTACGATACCGTTTGA

LYS CYS THR ALA SER ASN LYS ASN ARG GLY ILE ILE LYS THR PHE SER ASN GLY CYS ASP
AAATGTACAGCATCCAATAAAAATCGTGGAATCATAAAGACATTTCTAACGGGTGTGAT
     1270           1280           1290           1300           1310      1320
TTTACATGTCGTAGGTTATTTTTAGCACCTTAGTATTTCTGTAAAAGATTGCCCACACTA

TYR VAL SER ASN LYS GLY VAL ASP THR VAL SER VAL GLY ASN THR LEU TYR TYR VAL ASN
TATGTATCAAATAAAGGGGTGGACACTGTGTCTGTAGGTAACACATTATTATGTAAAT
     1330           1340           1350           1360           1370      1380
ATACATAGTTTATTTCCCACCTGTGACACAGATCCATTGTGTAATATAATACATTTA

LYS GLN GLU GLY LYS SER LEU TYR VAL LYS GLY GLU PRO ILE ILE ASN PHE TYR ASP PRO
AAGCAAGAAGGCAAAAGTCTCTATGTAAAAGGTGAACCAATAAJAAATTTCTATGACCCA
     1390           1400           1410           1420           1430      1440
TTCGTTCTTCCGTTTTCAGAGATACATTTCCACTTGGTATTATTTAAAGATACTGGGT

LEU VAL PHE PRO SER ASP GLU PHE ASP ALA SER ILE SER GLN VAL ASN GLU LYS ILE ASN
TTAGTATTCCCCTCTGATGAATTTGATGCATCAATATCTCAAGTCAATGAGAAGATTAAC
     1450           1460           1470           1480           1490      1500
AATCATAAGGGAGACTACTTAAACTACGTAGTTATAGAGTTCAGTTACTCTTCTAATTG

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGTAAA
     1510           1520           1530           1540           1550      1560
GTCTCAAATCGTAAATAAGCATTTAGGCTACTTAATAATGTATTACATTTACGACCATTT

SER THR ASN ILE MET Thr Stop Stop Stop Bam HI
TCAACCACAAATATCATGACTTGATAATGAGGATCC
AGTTGGTGTTTATAGTACTGAACTGAACTATTCCTAGG
     1570
```

FIG.8

```
401  TTGGGACCCC  TTGATTGTTC  TTTCTTTTTC  GCTATTGTAA  AATTCATGTT
451  ATATGGAGGG  GGCAAAGTTT  TCAGGGTGTT  GTTTAGAATG  GGAAGATGTC
501  CCTTGTATCA  CCATGGACCC  TCATGATAAT  TTTGTTTCTT  TCACTTTCTA
551  CTCTGTTGAC  AACCATGTC   TCCTCTTATT  TTCTTTTCAT  TTTCTGTAAC
601  TTTTTCGTTA  AACTTTAGCT  TGCATTTGTA  ACGAATTTTT  AAATTCACTT
651  TTGTTTATTT  GTCAGATTGT  AAGTACTTTC  TCTAATCACT  TTTTTTTCAA
701  GGCAATCAGG  GTATATTATA  TTGTACTTCA  GCACAGTTTT  AGAGAACAAT
751  TGTTATAATT  AAATGATAAG  GTAGAATATT  TCTGCATATA  AATTCTGGCT
801  GGCGTGGAAA  TATTCTTATT  GGTAGAAACA  ACTACATCCT  GGTCATCATC
851  CTGCCTTTCT  CTTTATGGTT  ACAATGATAT  ACACTGTTTG  AGATGAGGAT
901  AAAATACTCT  GAGTCCAAAC  CGGGCCCCCTC  TGCTAACCAT  GTTCATGCCT
951  TCTTCTTTTT  CCTACAG     GTGAGT
``` ature was performed and three doses of 50 μg were required

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1886 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATGGAGTTGC  CAATCCTCAA  AGCAAATGCA  ATTACCACAA  TCCTCGCTGC  AGTCACATTT     60
TGCTTTGCTT  CTAGTCAAAA  CATCACTGAA  GAATTTTATC  AATCAACATG  CAGTGCAGTT    120
AGCAAAGGCT  ATCTTAGTGC  TCTAAGAACT  GGTTGGTATA  CTAGTGTTAT  AACTATAGAA    180
TTAAGTAATA  TCAAGGAAAA  TAAGTGTAAT  GGAACAGATG  CTAAGGTAAA  ATTGATGAAA    240
CAAGAATTAG  ATAAATATAA  AAATGCTGTA  ACAGAATTGC  AGTTGCTCAT  GCAAAGCACA    300
CCAGCAGCAA  ACAATCGAGC  CAGAAGAGAA  CTACCAAGGT  TTATGAATTA  TACACTCAAC    360
AATACCAAAA  AAACCAATGT  AACATTAAGC  AAGAAAGGA   AAGAAGATT   TCTTGGTTTT    420
TTGTTAGGTG  TTGGATCTGC  AATCGCCAGT  GGCATTGCTG  TATCTAAGGT  CCTGCACTTA    480
GAAGGAGAAG  TGAACAAGAT  CAAAGTGCT   CTACTATCCA  CAAACAAGGC  CGTAGTCAGC    540
TTATCAAATG  GAGTTAGTGT  CTTAACCAGC  AAAGTGTTAG  ACCTCAAAAA  CTATATAGAT    600
AAACAATTGT  TACCTATTGT  GAATAAGCAA  AGCTGCAGAA  TATCAAATAT  AGAAACTGTG    660
ATAGAGTTCC  AACAAAGAA   CAACAGACTA  CTAGAGATTA  CCAGGGAATT  TAGTGTTAAT    720
GCAGGTGTAA  CTACACCTGT  AAGCACTTAC  ATGTTAACTA  ATAGTGAATT  ATTGTCATTA    780
ATCAATGATA  TGCCTATAAC  AAATGATCAG  AAAAAGTTAA  TGTCCAACAA  TGTTCAAATA    840
GTTAGACAGC  AAAGTTACTC  TATCATGTCC  ATAATAAAAG  AGGAAGTCTT  AGCATATGTA    900
GTACAATTAC  CACTATATGG  TGTGATAGAT  ACACCTTGTT  GGAAATTACA  CACATCCCCT    960
CTATGTACAA  CCAACACAAA  AGAAGGGTCA  AACATCTGTT  TAACAAGAAC  TGACAGAGGA   1020
TGGTACTGTG  ACAATGCAGG  ATCAGTATCT  TTCTTCCCAC  AAGCTGAAAC  ATGTAAAGTT   1080
CAATCGAATC  GAGTATTTTG  TGACACAATG  AACAGTTTAA  CATTACCAAG  TGAAGTAAAT   1140
CTCTGCAATG  TTGACATATT  CAATCCCAAA  TATGATTGTA  AAATTATGAC  TTCAAAAACA   1200
GATGTAAGCA  GCTCCGTTAT  CACATCTCTA  GGAGCCATTG  TGTCATGCTA  TGGCAAAACT   1260
AAATGTACAG  CATCCAATAA  AAATCGTGGA  ATCATAAAGA  CATTTTCTAA  CGGGTGTGAT   1320
TATGTATCAA  ATAAAGGGGT  GGACACTGTG  TCTGTAGGTA  ACACATTATA  TTATGTAAAT   1380
AAGCAAGAAG  GCAAAAGTCT  CTATGTAAAA  GGTGAACCAA  TAATAAATTT  CTATGACCCA   1440
TTAGTATTCC  CCTCTGATGA  ATTTGATGCA  TCAATATCTC  AAGTCAATGA  GAAGATTAAC   1500
CAGAGTTTAG  CATTTATTCG  TAAATCCGAT  GAATTATTAC  ATAATGTAAA  TGCTGGTAAA   1560
TCAACCACAA  ATATCATGAT  AACTACTATA  ATTATAGTGA  TTATAGTAAT  ATTGTTATCA   1620
TTAATTGCTG  TTGGACTGCT  CCTATACTGT  AAGGCCAGAA  GCACACCAGT  CACACTAAGC   1680
AAGGATCAAC  TGAGTGGTAT  AAATAATATT  GCATTTAGTA  ACTGAATAAA  AATAGCACCT   1740
AATCATGTTC  TTACAATGGT  TTACTATCTG  CTCATAGACA  ACCCATCTAT  CATTGGATTT   1800
TCTTAAAATC  TGAACTTCAT  CGAAACTCTT  ATCTATAAAC  CATCTCACTT  ACACTATTTA   1860
```

AGTAGATTCC TAGTTTATAG TTATAT                                                                                                                  1886

(2) INFORMATION FOR SEQ ID NO:2:

(i) SEQUENCE CHARACTERISTICS:
        (A) LENGTH: 594 amino acids
        (B) TYPE: amino acid
        (C) STRANDEDNESS: single
        (D) TOPOLOGY: linear (xi) SEQUENCE DESCRIPTION: SEQ ID NO:2:

```
Met Glu Leu Pro Ile Leu Lys Ala Asn Ala Ile Thr Thr Ile Leu Ala
 1               5                  10                 15

Ala Val Thr Phe Cys Phe Ala Ser Ser Gln Asn Ile Thr Glu Glu Phe
                20                  25                 30

Tyr Gln Ser Thr Cys Ser Ala Val Ser Lys Gly Tyr Leu Ser Ala Leu
            35                  40                 45

Arg Thr Gly Trp Tyr Thr Ser Val Ile Thr Ile Glu Leu Ser Asn Ile
        50                  55                 60

Lys Glu Asn Lys Cys Asn Gly Thr Asp Ala Lys Val Lys Leu Met Lys
65                  70                  75                 80

Gln Glu Leu Asp Lys Tyr Lys Asn Ala Val Thr Glu Leu Gln Leu Leu
                85                  90                 95

Met Gln Ser Thr Pro Ala Ala Asn Asn Arg Ala Arg Arg Glu Leu Pro
            100                 105                110

Arg Phe Met Asn Tyr Thr Leu Asn Asn Thr Lys Lys Thr Asn Val Thr
        115                 120                125

Leu Ser Lys Lys Arg Lys Arg Arg Phe Leu Gly Phe Leu Leu Gly Val
    130                 135                140

Gly Ser Ala Ile Ala Ser Gly Ile Ala Val Ser Lys Val Leu His Leu
145                 150                 155                160

Glu Gly Glu Val Asn Lys Ile Lys Ser Ala Leu Leu Ser Thr Asn Lys
                165                 170                175

Ala Val Val Ser Leu Ser Asn Gly Val Ser Val Leu Thr Ser Lys Val
            180                 185                190

Leu Asp Leu Lys Asn Tyr Ile Asp Lys Gln Leu Leu Pro Ile Val Asn
        195                 200                205

Lys Arg Ser Cys Arg Ile Ser Asn Ile Glu Thr Val Ile Glu Phe Gln
    210                 215                220

His Lys Asn Asn Arg Leu Leu Glu Ile Thr Arg Glu Phe Ser Val Asn
225                 230                 235                240

Ala Gly Val Thr Thr Pro Val Ser Thr Tyr Met Leu Thr Asn Ser Glu
                245                 250                255

Leu Leu Ser Leu Ile Asn Asp Met Pro Ile Thr Asn Asp Gln Lys Lys
            260                 265                270

Leu Met Ser Asn Asn Val Gln Ile Val Arg Gln Gln Ser Tyr Ser Ile
        275                 280                285

Met Ser Ile Ile Lys Glu Glu Val Leu Ala Tyr Val Val Gln Leu Pro
    290                 295                300

Leu Tyr Gly Val Ile Asp Thr Pro Cys Trp Lys Leu His Thr Ser Pro
305                 310                 315                320

Leu Cys Thr Thr Asn Thr Lys Glu Gly Ser Asn Ile Cys Leu Thr Arg
                325                 330                335

Thr Asp Arg Gly Trp Tyr Cys Asp Asn Ala Gly Ser Val Ser Phe Phe
            340                 345                350

Pro Gln Ala Glu Thr Cys Lys Val Gln Ser Asn Arg Val Phe Cys Asp
```

|       |       |       |       |       | 355   |       |       |       |       | 360   |       |       |       |       | 365   |       |       |
|---|---|---|---|---|---|---|---|---|---|---|---|---|---|---|---|---|---|
| Thr   | Met 370 | Asn   | Ser   | Leu   | Thr   | Leu 375 | Pro   | Ser   | Glu   | Val   | Asn 380 | Leu   | Cys   | Asn   | Val   |       |       |
| Asp 385 | Ile   | Phe   | Asn   | Pro   | Lys 390 | Tyr   | Asp   | Cys   | Lys   | Ile 395 | Met   | Thr   | Ser   | Lys   | Thr 400 |       |       |
| Asp   | Val   | Ser   | Ser   | Ser 405 | Val   | Ile   | Thr   | Ser   | Leu 410 | Gly   | Ala   | Ile   | Val   | Ser 415 | Cys   |       |       |
| Tyr   | Gly   | Lys   | Thr 420 | Lys   | Cys   | Thr   | Ala   | Ser 425 | Asn   | Lys   | Asn   | Arg   | Gly 430 | Ile   | Ile   |       |       |
| Lys   | Thr   | Phe 435 | Ser   | Asn   | Gly   | Cys   | Asp 440 | Tyr   | Val   | Ser   | Asn   | Lys 445 | Gly   | Val   | Asp   |       |       |
| Thr   | Val 450 | Ser   | Val   | Gly   | Asn   | Thr 455 | Leu   | Tyr   | Tyr   | Val   | Asn 460 | Lys   | Gln   | Glu   | Gly   |       |       |
| Lys 465 | Ser   | Leu   | Tyr   | Val   | Lys 470 | Gly   | Glu   | Pro   | Ile   | Ile 475 | Asn   | Phe   | Tyr   | Asp   | Pro 480 |       |       |
| Leu   | Val   | Phe   | Pro   | Ser 485 | Asp   | Glu   | Phe   | Asp   | Ala 490 | Ser   | Ile   | Ser   | Gln   | Val 495 | Asn   |       |       |
| Glu   | Lys   | Ile   | Asn 500 | Leu   | Val   | Phe   | Pro   | Ser 505 | Asp   | Glu   | Phe   | Asp   | Ala 510 | Ser   | Ile   |       |       |
| Ser   | Gln   | Val 515 | Asn   | Glu   | Lys   | Ile   | Asn 520 | Gln   | Ser   | Leu   | Ala   | Phe 525 | Ile   | Arg   | Lys   |       |       |
| Ser   | Asp 530 | Glu   | Leu   | Leu   | His   | Asn 535 | Val   | Asn   | Ala   | Gly   | Lys 540 | Ser   | Thr   | Thr   | Asn   |       |       |
| Ile 545 | Met   | Ile   | Thr   | Thr   | Ile 550 | Ile   | Ile   | Glu   | Ile   | Ile 555 | Val   | Ile   | Leu   | Leu   | Ser 560 |       |       |
| Leu   | Ile   | Ala   | Val   | Gly 565 | Leu   | Leu   | Leu   | Tyr   | Cys 570 | Lys   | Ala   | Arg   | Ser   | Thr 575 | Pro   |       |       |
| Val   | Thr   | Leu   | Ser 580 | Lys   | Asp   | Gln   | Leu   | Ser 585 | Gly   | Ile   | Asn   | Asn   | Ile 590 | Ala   | Phe   |       |       |
| Ser   | Asn   |       |       |       |       |       |       |       |       |       |       |       |       |       |       |       |       |

( 2 ) INFORMATION FOR SEQ ID NO:3:

( i ) SEQUENCE CHARACTERISTICS:
        ( A ) LENGTH: 1904 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | | |
|---|---|---|---|---|---|
| ATGGAGTTGC | CAATCCTCAA | AGCAAATGCA | ATTACCACAA | TCCTCGCTGC | AGTCACATTT | 60 |
| TGCTTTGCTT | CTAGTCAAAA | CATCACTGAA | GAATTTTATC | AATCAACATG | CAGTGCAGTT | 120 |
| AGCAAAGGCT | ATCTTAGTGC | TCTAAGAACT | GGTTGGTATA | CTAGTGTTAT | AACTATAGAA | 180 |
| TTAAGTAATA | TCAAGGAAAA | TAAGTGTAAT | GGAACAGATG | CTAAGGTAAA | ATTGATGAAA | 240 |
| CAAGAATTAG | ATAAATATAA | AAATGCTGTA | ACAGAATTGC | AGTTGCTCAT | GCAAAGCACA | 300 |
| CCAGCAGCAA | ACAATCGAGC | CAGAAGAGAA | CTACCAAGGT | TTATGAATTA | TACACTCAAC | 360 |
| AATACCAAAA | AAACCAATGT | AACATTAAGC | AAGAAAAGGA | AAAGAAGATT | TCTTGGTTTT | 420 |
| TTGTTAGGTG | TTGGATCTGC | AATCGCCAGT | GGCATTGCTG | TATCTAAGGT | CCTGCACTTA | 480 |
| GAAGGAGAAG | TGAACAAGAT | CAAAAGTGCT | CTACTATCCA | CAAACAAGGC | CGTAGTCAGC | 540 |
| TTATCAAATG | GAGTTAGTGT | CTTAACCAGC | AAAGTGTTAG | ACCTCAAAAA | CTATATAGAT | 600 |
| AAACAATTGT | TACCTATTGT | GAATAAGCAA | AGCTGCAGAA | TATCAAATAT | AGAAACTGTG | 660 |
| ATAGAGTTCC | AACAAAAGAA | CAACAGACTA | CTAGAGATTA | CCAGGGAATT | TAGTGTTAAT | 720 |

|   |   |   |   |   |   |   |   |   |   |   |   |
|---|---|---|---|---|---|---|---|---|---|---|---|
GCAGGTGTAA | CTACACCTGT | AAGCACTTAC | ATGTTAACTA | ATAGTGAATT | ATTGTCATTA | 780
ATCAATGATA | TGCCTATAAC | AAATGATCAG | AAAAGTTAA | TGTCCAACAA | TGTTCAAATA | 840
GTTAGACAGC | AAAGTTACTC | TATCATGTCC | ATAATAAAAG | AGGAAGTCTT | AGCATATGTA | 900
GTACAATTAC | CACTATATGG | TGTGATAGAT | ACACCTTGTT | GGAAATTACA | CACATCCCCT | 960
CTATGTACAA | CCAACACAAA | AGAAGGGTCA | AACATCTGTT | TAACAAGAAC | TGACAGAGGA | 1020
TGGTACTGTG | ACAATGCAGG | ATCAGTATCT | TTCTTCCCAC | AAGCTGAAAC | ATGTAAAGTT | 1080
CAATCGAATC | GAGTATTTTG | TGACACAATG | AACAGTTTAA | CATTACCAAG | TGAAGTAAAT | 1140
CTCTGCAATG | TTGACATATT | CAATCCCAAA | TATGATTGTA | AAATTATGAC | TTCAAAAACA | 1200
GATGTAAGCA | GCTCCGTTAT | CACATCTCTA | GGAGCCATTG | TGTCATGCTA | TGGCAAAACT | 1260
AAATGTACAG | CATCCAATAA | AAATCGTGGA | ATCATAAAGA | CATTTTCTAA | CGGGTGTGAT | 1320
TATGTATCAA | ATAAAGGGGT | GGACACTGTG | TCTGTAGGTA | ACACATTATA | TTATGTAAAT | 1380
AAGCAAGAAG | GCAAAAGTCT | CTATGTAAAA | GGTGAACCAA | TAATAAATTT | CTATGACCCA | 1440
TTAGTATTCC | CCTCTGATGA | ATTTGATGCA | TCAATATCTC | AAGTCAATGA | GAAGATTAAC | 1500
CAGAGTTTAG | CATTTATTCG | TAAATCCGAT | GAATTATTAC | ATAATGTAAA | TGCTGGTAAA | 1560
TCAACCACAA | ATATCATGAC | TTGATAATGA | GGATCCATAA | CTACTATAAT | TATAGTGATT | 1620
ATAGTAATAT | TGTTATCATT | AATTGCTGTT | GGACTGCTCC | TATACTGTAA | GGCCAGAAGC | 1680
ACACCAGTCA | CACTAAGCAA | GGATCAACTG | AGTGGTATAA | ATAATATTGC | ATTTAGTAAC | 1740
TGAATAAAAA | TAGCACCTAA | TCATGTTCTT | ACAATGGTTT | ACTATCTGCT | CATAGACAAC | 1800
CCATCTATCA | TTGGATTTTC | TTAAAATCTG | AACTTCATCG | AAACTCTTAT | CTATAAACCA | 1860
TCTCACTTAC | ACTATTTAAG | TAGATTCCTA | GTTTATAGTT | ATAT |   | 1904

( 2 ) INFORMATION FOR SEQ ID NO:4:

( i ) SEQUENCE CHARACTERISTICS:
        ( A ) LENGTH: 527 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Met Glu Leu Pro Ile Leu Lys Ala Asn Ala Ile Thr Thr Ile Leu Ala
 1               5                  10                  15

Ala Val Thr Phe Cys Phe Ala Ser Ser Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Met Lys
 65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
```

|     |     |     |     | 145 |     |     |     |     | 150 |     |     |     |     | 155 |     |     |     |     | 160 |
|-----|-----|-----|-----|-----|-----|-----|-----|-----|-----|-----|-----|-----|-----|-----|-----|-----|-----|-----|-----|
| Glu | Gly | Glu | Val | Asn | Lys | Ile | Lys | Ser | Ala | Leu | Leu | Ser | Thr | Asn | Lys |
|     |     |     |     | 165 |     |     |     |     | 170 |     |     |     |     | 175 |     |
| Ala | Val | Val | Ser | Leu | Ser | Asn | Gly | Val | Ser | Val | Leu | Thr | Ser | Lys | Val |
|     |     |     | 180 |     |     |     |     | 185 |     |     |     |     | 190 |     |     |
| Leu | Asp | Leu | Lys | Asn | Tyr | Ile | Asp | Lys | Gln | Leu | Leu | Pro | Ile | Val | Asn |
|     |     | 195 |     |     |     |     | 200 |     |     |     |     | 205 |     |     |     |
| Lys | Gln | Ser | Cys | Arg | Ile | Ser | Asn | Ile | Glu | Thr | Val | Ile | Glu | Phe | Gln |
|     | 210 |     |     |     |     | 215 |     |     |     |     | 220 |     |     |     |     |
| His | Lys | Asn | Asn | Arg | Leu | Leu | Glu | Ile | Thr | Arg | Glu | Phe | Ser | Val | Asn |
| 225 |     |     |     |     | 230 |     |     |     |     | 235 |     |     |     |     | 240 |
| Ala | Gly | Val | Thr | Thr | Pro | Val | Ser | Thr | Tyr | Met | Leu | Thr | Asn | Ser | Glu |
|     |     |     |     | 245 |     |     |     |     | 250 |     |     |     |     | 255 |     |
| Leu | Leu | Ser | Leu | Ile | Asn | Asp | Met | Pro | Ile | Thr | Asn | Asp | Gln | Lys | Lys |
|     |     |     | 260 |     |     |     |     | 265 |     |     |     |     | 270 |     |     |
| Leu | Met | Ser | Asn | Asn | Val | Gln | Ile | Val | Arg | Gln | Gln | Ser | Tyr | Ser | Ile |
|     |     | 275 |     |     |     |     | 280 |     |     |     |     | 285 |     |     |     |
| Met | Ser | Ile | Ile | Lys | Glu | Glu | Val | Leu | Ala | Tyr | Val | Val | Gln | Leu | Pro |
|     | 290 |     |     |     |     | 295 |     |     |     |     | 300 |     |     |     |     |
| Leu | Tyr | Gly | Val | Ile | Asp | Thr | Pro | Cys | Trp | Lys | Leu | His | Thr | Ser | Pro |
| 305 |     |     |     |     | 310 |     |     |     |     | 315 |     |     |     |     | 320 |
| Leu | Cys | Thr | Thr | Asn | Thr | Lys | Glu | Gly | Ser | Asn | Ile | Cys | Leu | Thr | Arg |
|     |     |     |     | 325 |     |     |     |     | 330 |     |     |     |     | 335 |     |
| Thr | Asp | Arg | Gly | Trp | Tyr | Cys | Asp | Asn | Ala | Gly | Ser | Val | Ser | Phe | Phe |
|     |     |     | 340 |     |     |     |     | 345 |     |     |     |     | 350 |     |     |
| Pro | Gln | Ala | Glu | Thr | Cys | Lys | Val | Gln | Ser | Asn | Arg | Val | Phe | Cys | Asp |
|     |     | 355 |     |     |     |     | 360 |     |     |     |     | 365 |     |     |     |
| Thr | Met | Asn | Ser | Leu | Thr | Leu | Pro | Ser | Glu | Val | Asn | Leu | Cys | Asn | Val |
|     | 370 |     |     |     |     | 375 |     |     |     |     | 380 |     |     |     |     |
| Asp | Ile | Phe | Asn | Pro | Lys | Tyr | Asp | Cys | Lys | Ile | Met | Thr | Ser | Lys | Thr |
| 385 |     |     |     |     | 390 |     |     |     |     | 395 |     |     |     |     | 400 |
| Asp | Val | Ser | Ser | Ser | Val | Ile | Thr | Ser | Leu | Gly | Ala | Ile | Val | Ser | Cys |
|     |     |     |     | 405 |     |     |     |     | 410 |     |     |     |     | 415 |     |
| Tyr | Gly | Lys | Thr | Lys | Cys | Thr | Ala | Ser | Asn | Lys | Asn | Arg | Gly | Ile | Ile |
|     |     |     | 420 |     |     |     |     | 425 |     |     |     |     | 430 |     |     |
| Lys | Thr | Phe | Ser | Asn | Gly | Cys | Asp | Tyr | Val | Ser | Asn | Lys | Gly | Val | Asp |
|     |     | 435 |     |     |     |     | 440 |     |     |     |     | 445 |     |     |     |
| Thr | Val | Ser | Val | Gly | Asn | Thr | Leu | Tyr | Tyr | Val | Asn | Lys | Gln | Glu | Gly |
|     | 450 |     |     |     |     | 455 |     |     |     |     | 460 |     |     |     |     |
| Lys | Ser | Leu | Tyr | Val | Lys | Gly | Glu | Pro | Ile | Ile | Asn | Phe | Tyr | Asp | Pro |
| 465 |     |     |     |     | 470 |     |     |     |     | 475 |     |     |     |     | 480 |
| Leu | Val | Phe | Pro | Ser | Asp | Glu | Phe | Asp | Ala | Ser | Ile | Ser | Gln | Val | Asn |
|     |     |     |     | 485 |     |     |     |     | 490 |     |     |     |     | 495 |     |
| Glu | Lys | Ile | Asn | Gln | Ser | Leu | Ala | Phe | Ile | Arg | Lys | Ser | Asp | Glu | Leu |
|     |     |     | 500 |     |     |     |     | 505 |     |     |     |     | 510 |     |     |
| Leu | His | Asn | Val | Asn | Ala | Gly | Lys | Ser | Thr | Thr | Asn | Ile | Met | Thr |     |
|     |     | 515 |     |     |     |     | 520 |     |     |     |     | 525 |     |     |     |

( 2 ) INFORMATION FOR SEQ ID NO:5:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | | | |
|---|---|---|---|---|---|---|
| GTGAGTTTGG | GGACCCTTGA | TTGTTCTTTC | TTTTTCGCTA | TTGTAAAATT | CATGTTATAT | 60 |
| GGAGGGGGCA | AAGTTTTCAG | GGTGTTGTTT | AGAATGGGAA | GATGTCCCTT | GTATCACCAT | 120 |
| GGACCCTCAT | GATAATTTTG | TTTCTTTCAC | TTTCTACTCT | GTTGACAACC | ATTGTCTCCT | 180 |
| CTTATTTTCT | TTTCATTTTC | TGTAACTTTT | TCGTTAAACT | TTAGCTTGCA | TTTGTAACGA | 240 |
| ATTTTTAAAT | TCACTTTTGT | TTATTTGTCA | GATTGTAAGT | ACTTCTCTA | ATCACTTTTT | 300 |
| TTTCAAGGCA | ATCAGGGTAT | ATTATATTGT | ACTTCAGCAC | AGTTTTAGAG | AACAATTGTT | 360 |
| ATAATTAAAT | GATAAGGTAG | AATATTTCTG | CATATAAATT | CTGGCTGGCG | TGGAAATATT | 420 |
| CTTATTGGTA | GAAACAACTA | CATCCTGGTC | ATCATCCTGC | CTTTCTCTTT | ATGGTTACAA | 480 |
| TGATATACAC | TGTTTGAGAT | GAGGATAAAA | TACTCTGAGT | CCAAACCGGG | CCCCTCTGCT | 540 |
| AACCATGTTC | ATGCCTTCTT | CTTTTTCCTA | CAG | | | 573 |

NUCLEIC ACID RESPIRATORY SYNCYTIAL VIRUS VACCINES

This is a divisional of application Ser. No. 08/476,397 filed Jun. 7, 1995.

FIELD OF INVENTION

The present invention is related to the field of Respiratory Syncytial Virus (RSV) vaccines and is particularly concerned with vaccines comprising nucleic acid sequences encoding the fusion (F) protein of RSV.

BACKGROUND OF INVENTION

Respiratory syncytial virus (RSV), a negative-strand RNA virus belonging to the Paramyxoviridae family of viruses, is the major viral pathogen responsible for bronchiolitis and pneumonia in infants and young children (ref. 1). Throughout this application, various references are referred to in parenthesis to more fully describe the state of the art to which this invention pertains. Full bibliographic information for each immediately preceding the claims. The disclosures of these references are hereby incorporated by reference into the present disclosure). Acute respiratory tract infections caused by RSV result in approximately 90,000 hospitalizations and 4,500 deaths per year in the United States (ref. 2). Medical care costs due to RSV infection are greater than $340 M annually in the United States alone (ref. 3). There is currently no licensed vaccine against RSV. The main approaches for developing an RSV vaccine have included inactivated virus, live-attenuated viruses and subunit vaccines.

The F protein of RSV is considered to be one of the most important protective antigens of the virus. There is a significant similarity (89% identity) in the amino acid sequences of the F proteins from RSV subgroups A and B (ref. 3) and anti-F antibodies can cross-neutralize viruses of both subgroups as well as protect immunized animals against infection with viruses from both subgroups (ref. 4). Furthermore, the F protein has been identified as a major target for RSV-specific cytotoxic T-lymphocytes in mice and humans (ref. 3 and ref. 5).

The use of RSV proteins as vaccines may have obstacles. Parenterally administered vaccine candidates of these types have proven poorly immunogenic with regard to the induction of neutralizing antibodies in seronegative humans or chimpanzees. The serum antibody response induced by these antigens may be further diminished in the presence of passively acquired antibodies, such as the transplacentally acquired maternal antibodies which most young infants possess. A subunit vaccine candidate for RSV consisting of purified fusion glycoprotein from RSV infected cell cultures and purified by immunoaffinity or ion-exchange chromatography has been described (ref. 6). Parenteral immunization of seronegative or seropositive chimpanzees with this preparation was performed and three doses of 50 μg were required in seronegative animals to induce RSV serum neutralizing titre of approximately 1:50. Upon subsequent challenge of these animals with wild-type RSV, no effect of immunization on virus shedding or clinical disease could be detected in the upper respiratory tract. The effect of immunization with this vaccine on virus shedding in the lower respiratory tract was not investigated, although this is the site where the serum antibody induced by parenteral immunization may be expected to have its greatest effect.

Ten safety and immunogenicity studies have been performed in a small number of seropositive individuals. This vaccine was found to be safe in seropositive children and in three seronegative children (all >2.4 years of age). The effects of immunization on lower respiratory disease could not be determined because of the small number of children immunized. One immunizing dose in seropositive children induced a 4-fold increase in virus neutralizing antibody titres in 40 to 60% of the vaccinees. Thus, insufficient information is available from these small studies to evaluate the efficacy of this vaccine against RSV-induced disease. A further problem facing subunit RSV vaccines is the possibility that inoculation of seronegative subjects with immunogenic preparations might result in disease enhancement (sometimes referred to as immunopotentiation), similar to that seen in formalin inactivated RSV vaccines. In some studies, the immune response to immunization with RSV F protein or a synthetic RSV FG fusion protein resulted in a disease enhancement in rodents resembling that induced by a formalin-inactivated RSV vaccine. The association of immunization with disease enhancement using non-replicating antigens suggests caution in their use as vaccines in seronegative humans.

Live attenuated vaccines against disease caused by RSV may be promising for two main reasons. First, infection by a live vaccine virus induces a balanced immune response comprising mucosal and serum antibodies and cytolytic T-lymphocytes. Second, primary infection of infants with live attenuated vaccine candidates or naturally acquired wild-type virus is not associated with enhanced disease upon subsequent natural reinfection. It will be challenging to produce live attenuated vaccines that are immunogenic for younger infants who possess maternal virus-neutralizing antibodies and yet are attenuated for seronegative infants greater than or equal to 6 months. Attenuated live virus vaccines also have the risks of residual virulence and genetic instability.

Injection of plasmid DNA containing sequences encoding a foreign protein has been shown to result in expression of the foreign protein and the induction of antibody and cytotoxic T-lymphocyte responses to the antigen in a number of studies (see, for example, refs. 7, 8, 9). The use of plasmid DNA inoculation to express viral proteins for the purpose of immunization may offer several advantages over the strategies summarized above. Firstly, DNA encoding a viral antigen can be introduced in the presence of antibody to the virus itself, without loss of potency due to neutralization of virus by the antibodies. Secondly, the antigen expressed in vivo should exhibit a native conformation and, therefore, should induce an antibody response similar to that induced by the antigen present in the wild-type virus infection. In contrast, processes used in purification of proteins can induce conformational changes which may result in the loss of immunogenicity of protective epitopes and possibly immunopotentiation. Thirdly, the expression of proteins from injected plasmid DNAs can be detected in vivo for a considerably longer period of time than that in virus-infected cells, and this has the theoretical advantage of prolonged cytolytic T-cell and enhanced antibody responses. Fourthly, in vivo expression of antigen may provide protection without the need for extrinsic adjuvant.

The ability to immunize against disease caused by RSV by administration of a DNA molecule encoding an RSV F protein was unknown before the present invention. In particular, the efficacy of immunization against RSV induced disease using a gene encoding a secreted form of the RSV F protein was unknown. It would be useful and desirable to provide isolated genes encoding RSV F protein and vectors for in vivo administration for use in immunogenic preparations, including vaccines, for protection against disease caused by RSV and for the generation of diagnostic reagents and kits. In particular, it would be desirable to provide vaccines that are immunogenic and protective in humans, including seronegative infants, that do not cause disease enhancement.

SUMMARY OF INVENTION

The present invention relates to a method of immunizing a host against disease caused by respiratory syncytial virus, to nucleic acid molecules used therein, and to diagnostic procedures utilizing the nucleic acid molecules. In particular, the present invention is directed towards the provision of nucleic acid respiratory syncytial virus vaccines.

In accordance with one aspect of the invention, there is provided a vector, comprising:
   a first nucleotide sequence encoding a RSV F protein or a protein capable of generating antibodies that specifically react with RSV F protein;
   a promoter sequence operatively coupled to the first nucleotide sequence for expression of the RSV F protein, and
   a second nucleotide sequence located adjacent the first nucleotide sequence to enhance the immunoprotective ability of the RSV F protein when expressed in vivo from the vector in a host.

The first nucleotide sequence may be that which encodes a full-length RSV F protein, as seen in FIG. 2 (SEQ ID No: 2). Alternatively, the first nucleotide sequence may be that which encodes a RSV F protein from which the transmembrane region is absent. The latter embodiment may be provided by a nucleotide sequence which encodes a full-length RSV F protein but contains a translational stop codon immediately upstream of the start of the transmembrane coding region, thereby preventing expression of a transmembrane region of the RSV F protein, as seen in FIG. 3 (SEQ. ID No. 4). The lack of expression of the transmembrane region results in a secreted form of the RSV F protein.

The second nucleotide sequence may comprise a pair of splice sites to prevent aberrant mRNA splicing, whereby substantially all mRNA encodes the RSV protein. Such second nucleotide sequence may be located between the first nucleotide sequence and the promoter sequence. Such second nucleotide sequence preferably is that of rabbit β-globin intron II, as shown in FIG. 8 (SEQ ID No: 5).

A vector encoding the F protein and provided by this aspect of the invention may specifically be pXL2 or pXL4, as seen in FIGS. 5 or 7.

The promoter sequence preferably is an immediate early cytomegalovirus (CMV) promoter. Such cytomegalovirus promoter has not previously been employed in vectors containing nucleotide sequences encoding an RSV F protein. Accordingly, in another aspect of the invention, there is provided a vector, comprising:
   a first nucleotide sequence encoding a RSV F protein or a protein capable of generating antibodies that specifically react with RSV F protein, and
   a cytomegalovirus promoter operatively coupled to the first nucleotide sequence for expression of the RSV F protein.

The first nucleotide sequence may be any of the alternatives described above. The second nucleotide sequence described above also may be present in a vector provided in accordance with this second aspect of the invention.

Certain of the vectors provided herein may be used to immunize a host against RSV infection or disease using RSV F protein lacking a transmembrane region. In accordance with a further aspect of the present invention, therefore, there is provided a method of immunizing a host against disease caused by infection with respiratory syncytial virus, which comprises administering to the host an effective amount of a vector comprising a first nucleotide sequence encoding an RSV F or an RSV F protein lacking a transmembrane region and a promoter sequence operatively coupled to the first nucleotide sequence for expression of the RSV F protein in the host, which may be a human host. The promoter preferably is an immediate early cytomegalovirus promoter.

The nucleotide sequence encoding the truncated RSV F protein may be that as described above.

A vector containing a second nucleotide sequence located adjacent a first nucleotide sequence encoding an RSV F protein and effective to enhance the immunoprotective ability of the RSV F protein expressed by the first nucleotide sequence may be used to immunize a host. Accordingly, in an additional aspect of the present invention, there is provided a method of immunizing a host against disease caused by infection with respiratory syncytial virus (RSV), which comprises administering to the host an effective amount of a vector comprising a first nucleotide sequence encoding an RSV F protein or a protein capable of generating antibodies that specifically react with RSV F protein, a promoter sequence operatively coupled to the first nucleotide sequence for expression of the RSV F protein, and a second nucleotide sequence located adjacent the first sequence to enhance the immunoprotective ability of the RSV-F protein when expressed in vivo from said vector in said host. Specific vectors which may be used in this aspect of the invention are those identified as pXL2 and pXL4 in FIGS. 5 and 7.

The present invention also includes a novel method of using a gene encoding an RSV F protein or a protein capable of generating antibodies that specifically react with RSV F protein to protect a host against disease caused by infection with respiratory syncytial virus, which comprises:
   isolating the gene,
   operatively linking the gene to .at least one control sequence to produce a vector, said control sequence directing expression of the RSV F protein when introduced into a host to produce an immune response to the RSV F protein, and
   introducing the vector into a host.
The procedure provided in accordance with this aspect of the invention may further include the step of:
   operatively linking the gene to an immunoprotection enhancing sequence to produce an enhanced immunoprotection to the RSV F protein in the host, preferably by introducing the immunoprotection enhancing sequence between the control sequence and the gene.
In addition, the present invention includes a method of producing a vaccine for protection of a host against disease caused by infection with respiratory syncytial virus, which comprises:
   isolating a first nucleotide sequence encoding an RSV F protein or a protein capable of generating antibodies that specifically react with RSV F protein,
   operatively linking the first nucleotide sequence to at least one control sequence to produce a vector, the control sequence directing expression of the RSV F protein when introduced to a host to produce an immune response to the RSV F protein, and
   formulating the vector as a vaccine for in vivo administration to a host.

The first nucleotide sequence further may be operatively linked to a second nucleotide sequence to enhance the immunoprotective ability of the RSV F protein when expressed in vivo from the vector in a host. The vector may be selected from pXL1, pXL2 and pXL4. The invention further includes a vaccine for administration to a host, including a human host, produced by this method as well as immunogenic compositions comprising an immunoeffective amount of the vectors described herein.

As noted previously, the vectors provided herein are useful in diagnostic applications. In a further aspect of the invention, therefore, there is provided a method of determining the presence of an RSV F protein in a sample, comprising the steps of:

(a) immunizing a host with a vector comprising a first nucleotide sequence encoding an RSV F protein or a protein capable of generating antibodies that specifically react with RSV F protein and a promoter sequence operatively coupled to the first nucleotide sequence for expression of the RSV F protein in the host to produce antibodies specific to the RSV F protein;

(b) isolating the RSV F protein specific antibodies;

(c) contacting the sample with the isolated antibodies to produce complexes comprising any RSV F protein present in a sample and the RSV F protein-specific antibodies; and (d) determining the production of the complexes.

The vector employed to elicit the antibodies may be pXL1, pXL2, pXL3 or pXL4.

The invention also includes a diagnostic kit for detecting the presence of an RSV F protein in a sample, comprising:

(a) a vector comprising a first nucleotide sequence encoding an RSV F protein capable of generating antibodies that specifically react with RSV F protein and a promoter sequence operatively coupled to said first nucleotide sequence for expression of said RSV F protein in a host immunized therewith;

(b) means for contacting the RSV F specific antibodies with the sample to produce a complex comprising any RSV F protein in the sample and RSV F protein specific antibodies, and (c) means for determining production of the complex.

The present invention is further directed to immunization wherein the polynucleotide is an RNA molecule which codes for an RSV F protein.

The present invention is further directed to a method for producing polyclonal antibodies comprising the use of the immunization method described herein, and further comprising the step of isolating the polyclonal antibodies from the immunized animal.

The present invention is also directed to a method for producing monoclonal antibodies comprising the steps of:

(a) constructing a vector comprising:
   a first nucleotide sequence encoding a RSV F protein;
   a promoter sequence operatively coupled to said first nucleotide sequence for expression of said RSV F protein; and, optionally,
   a second nucleotide sequence located adjacent said first nucleotide sequence to enhance the immunoprotective ability of said RSV F protein when expressed in vivo from said vector in a host.

(b) administering the vector to at least one mouse to produce at least one immunized mouse;

(c) removing B-lymphocytes from the at least one immunized mouse;

(d) fusing the B-lymphocytes from the at least one immunized mouse with myeloma cells, thereby producing hybridomas;

(e) cloning the hybridomas;

(f) selecting clones which produce anti-F protein antibody;

(g) culturing the anti-F protein antibody-producing clones; and then (h) isolating anti-F protein antibodies.

In this application, the term "RSV F protein" is used to define a full-length RSV F protein, secreted form of RSV F protein lacking a transmembrane region, such proteins having variations in their amino acid sequences including those naturally occurring in various strains of RSV, as well as functional analogs of the RSV F protein. In this application, a first protein is a "functional analog" of a second protein if the first protein is immunologically related to and/or has the same function as the second protein. The functional analog may be, for example, a fragment of the protein or a substitution, addition or deletion mutant thereof.

BRIEF DESCRIPTION OF THE FIGURES

The present invention will be further understood from the following general description and Examples with reference to the Figures in which:

FIG. 1 illustrates a restriction map of the gene encoding the F protein of Respiratory Syncytial Virus;

FIGS. 2A, 2B, 2C, 2D and 2E show the nucleotide sequence of the gene encoding the membrane attached form of the F protein of Respiratory Syncytial Virus (SEQ ID No: 1) as well as the amino acid sequence of the RSV F protein encoded thereby (SEQ ID No: 2);

FIGS. 3A, 3B, 3C and 3D show the nucleotide sequence of the gene encoding the secreted form of the RSV F protein (SEQ ID No: 3) as well as the amino acid sequence of the truncated RSV F protein encoded thereby (SEQ ID No: 4);

FIG. 8 shows the nucleotide sequence for the rabbit β-globin Intron II sequence (SEQ ID No. 5).

GENERAL DESCRIPTION OF INVENTION

As described above, the present invention relates generally to DNA immunization to obtain protection against infection by respiratory syncytial virus and to diagnostic procedures using particular vectors. In the present invention, several recombinant vectors are constructed to contain a nucleotide sequence encoding an RSV F protein.

Figure 2A:
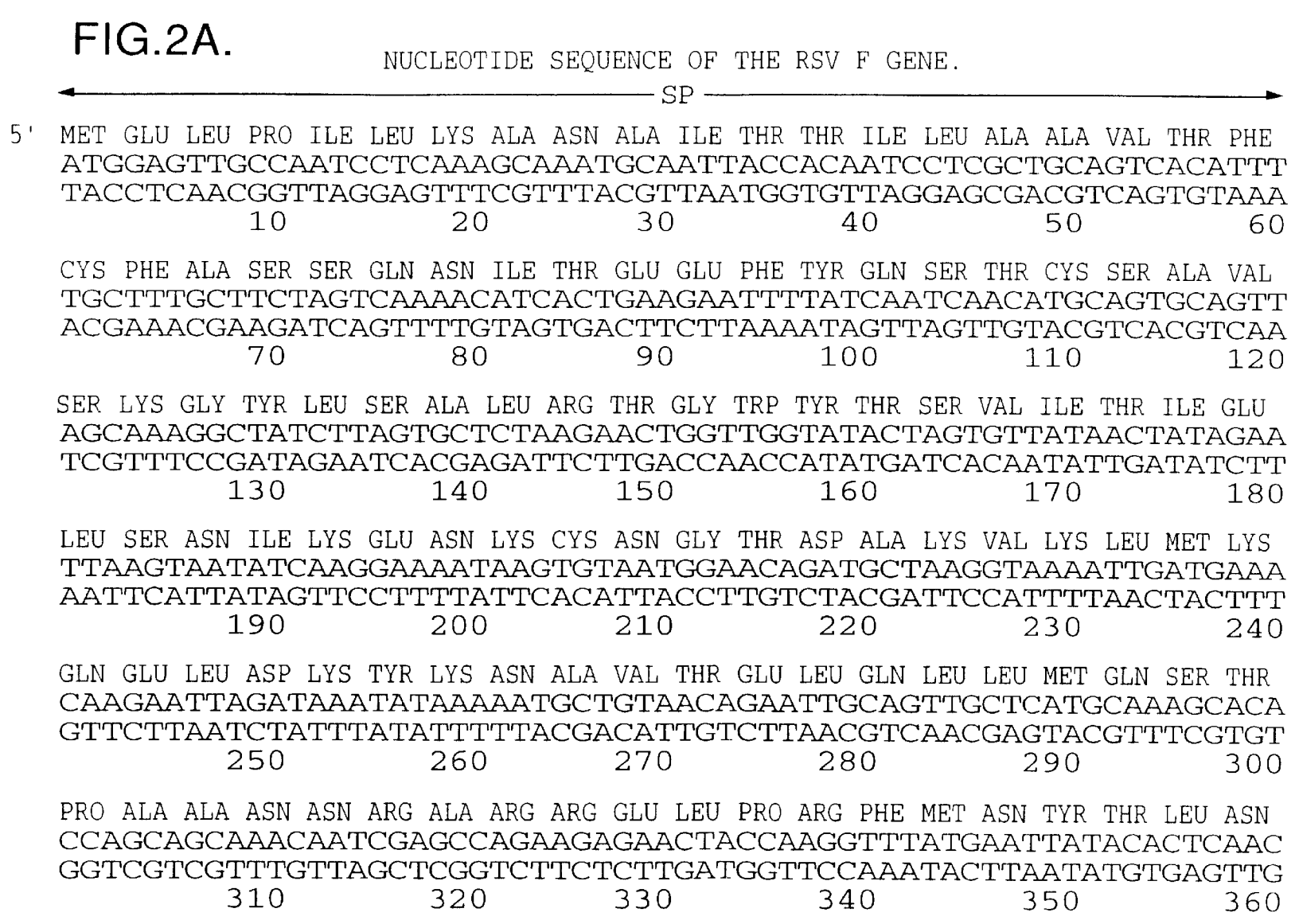

The nucleotide sequence of the RSV F gene is shown in FIG. 2 (SEQ ID No: 1). Certain constructs provided herein include the nucleotide sequence encoding the full-length RSV F protein while others include an RSV F gene modified by insertion of termination codons immediately upstream of the transmembrane coding region (see FIG. 3, SEQ ID No: 3), to prevent expression of the transmembrane portion of the protein and to produce a secreted or truncated RSV F protein.

The nucleotide sequence encoding the RSV F protein is operatively coupled to a promoter sequence for expression of the encoded RSV F protein. The promoter sequence may be the immediately early cytomegalovirus (CMV) promoter. This promoter is described in ref. 13. Any other convenient promoter may be used, including constitutive promoters, such as, Rous Sarcoma Virus LTRs, and inducible promoters, such as metallothionine promoter, and tissue specific promoters.

Figure 4A:
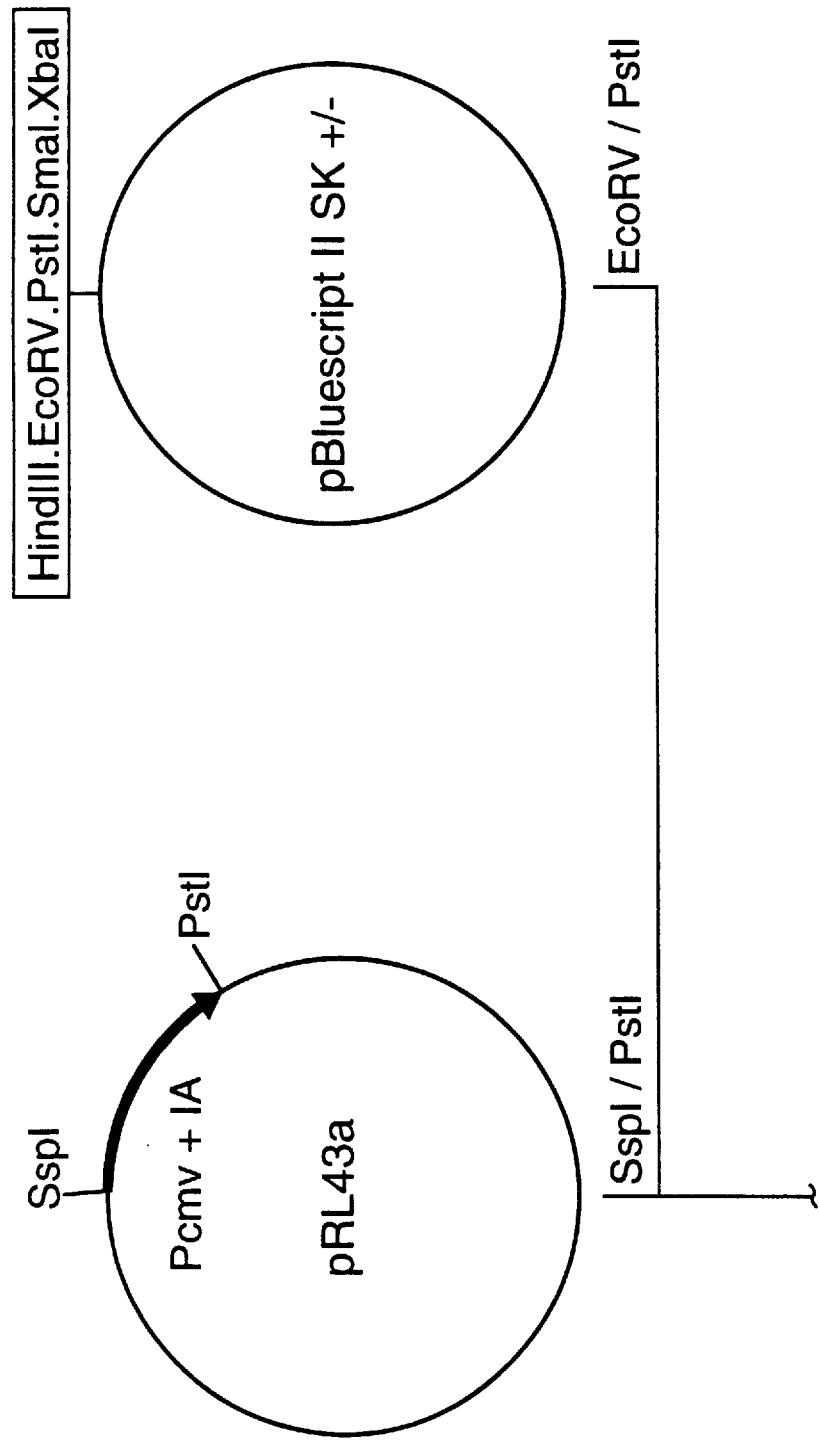
FIGS. 4A–4D show the construction of plasmid pXL1 containing the gene encoding a secreted form of the RSV F protein.
Figure 4B:
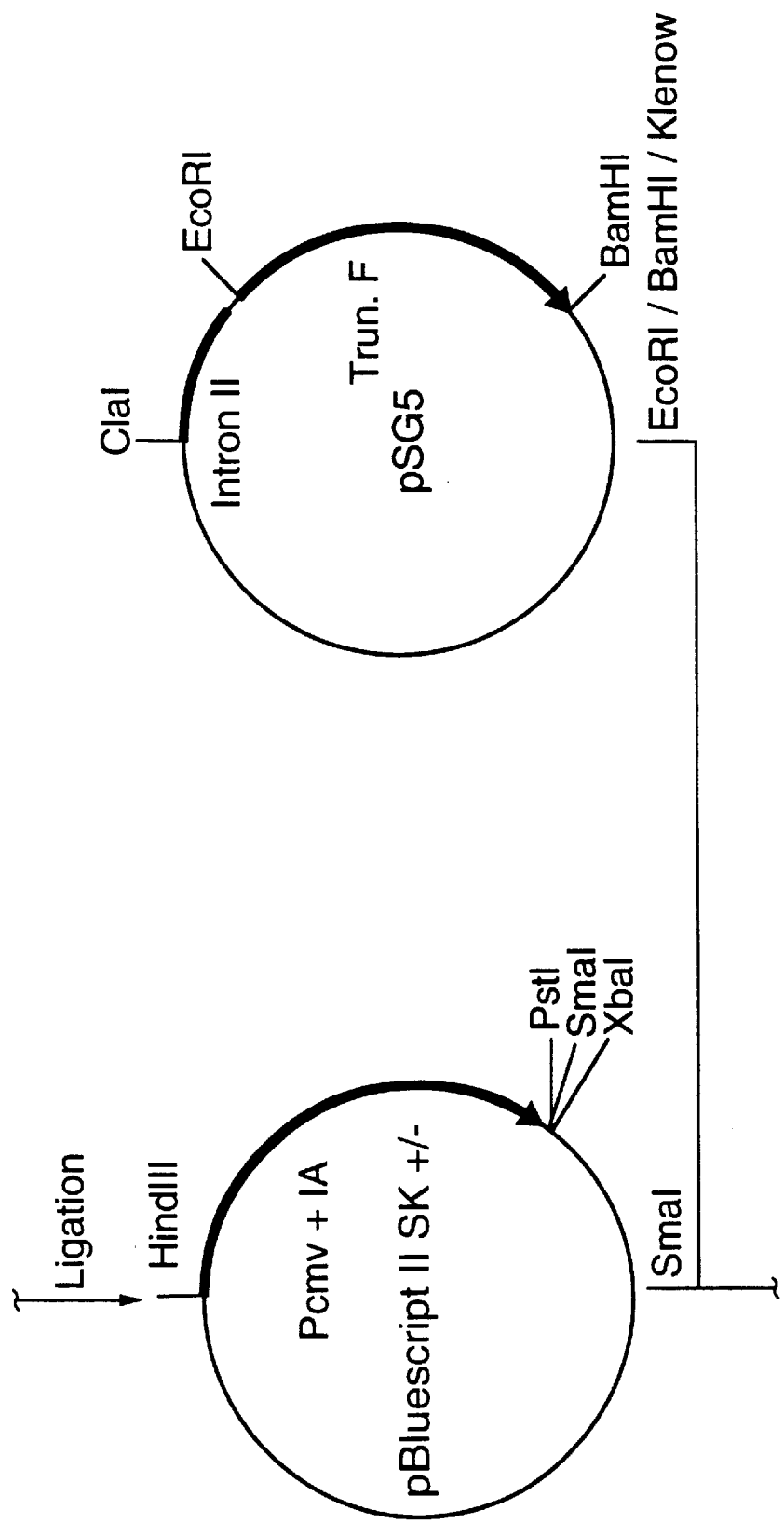
Figure 4C:
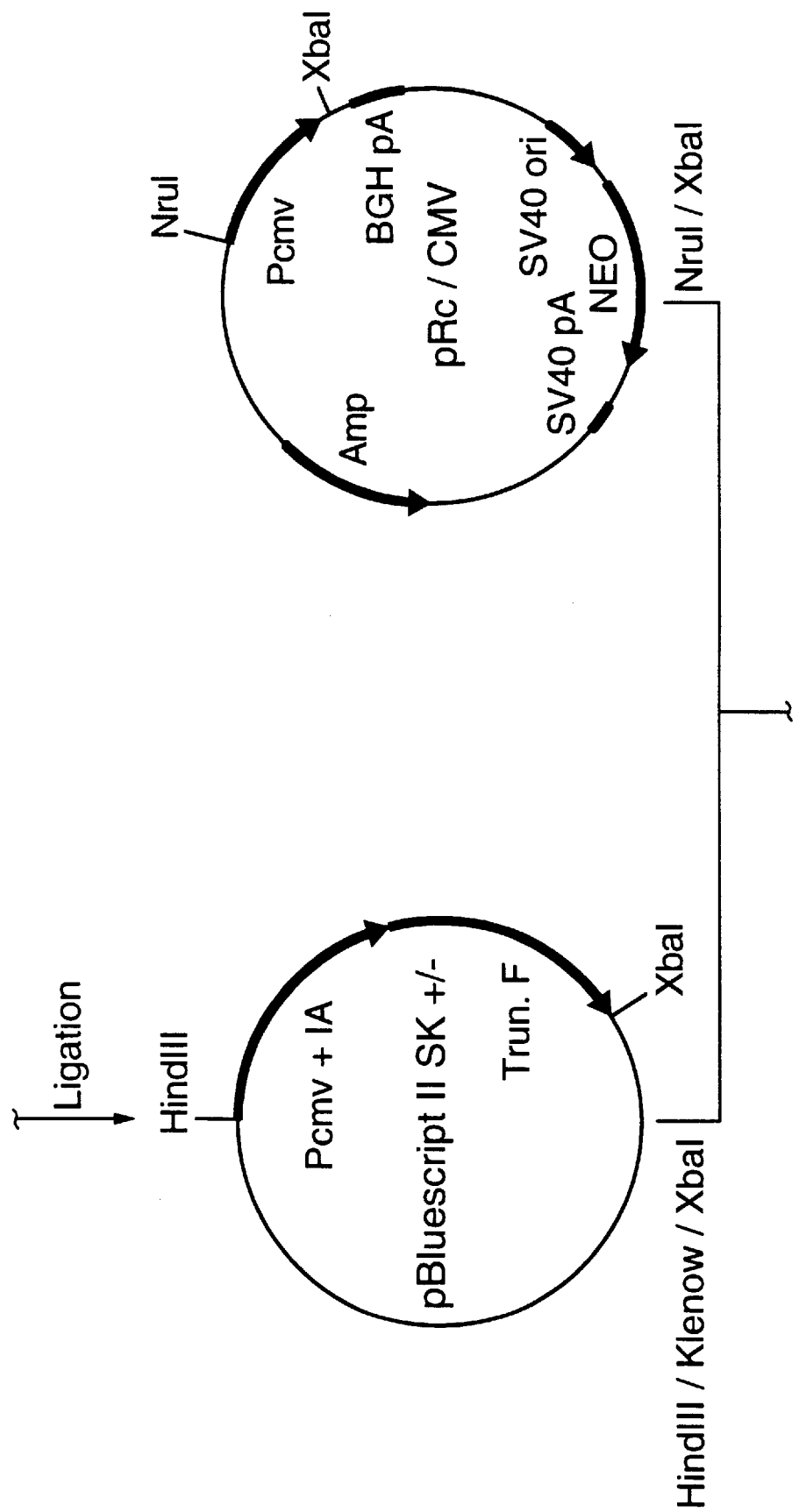
Figure 4D:
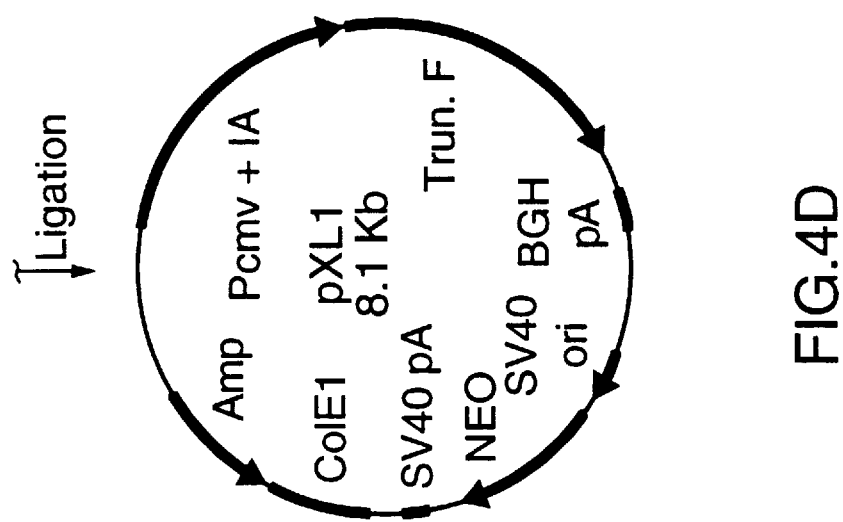

The vector, when administered to an animal, effects in vivo RSV F protein expression, as demonstrated by an antibody response in the animal to which it is administered. Such antibodies may be used herein in the detection of RSV protein in a sample, as described in more detail below. When the encoded RSV F protein is in the form of an RSV F protein from which the transmembrane region is absent, such as plasmid pXL1 (FIG. 4), the administration of the vector conferred protection in mice to challenge by live RSV, as seen from the Examples below.

The recombinant vector also may include a second nucleotide sequence located adjacent the RSV F protein encoding nucleotide sequence to enhance the immunoprotective ability of the RSV F protein when expressed in vivo in a host. Such enhancement may be provided by increased in vivo expression, for example, by increased mRNA stability, enhanced transcription and/or translation. This additional sequence preferably is located between the promoter sequence and the RSV F protein-encoding sequence.

This enhancement sequence may comprise a pair of splice sites to prevent aberrant mRNA splicing during transcription and translation so that substantially all mRNA encodes an RSV F protein. Specifically, rabbit β-globin Intron II sequence shown in FIG. 8 (SEQ ID No: 5) may provide such splice sites, as also described in ref. 15.

Figure 5A:
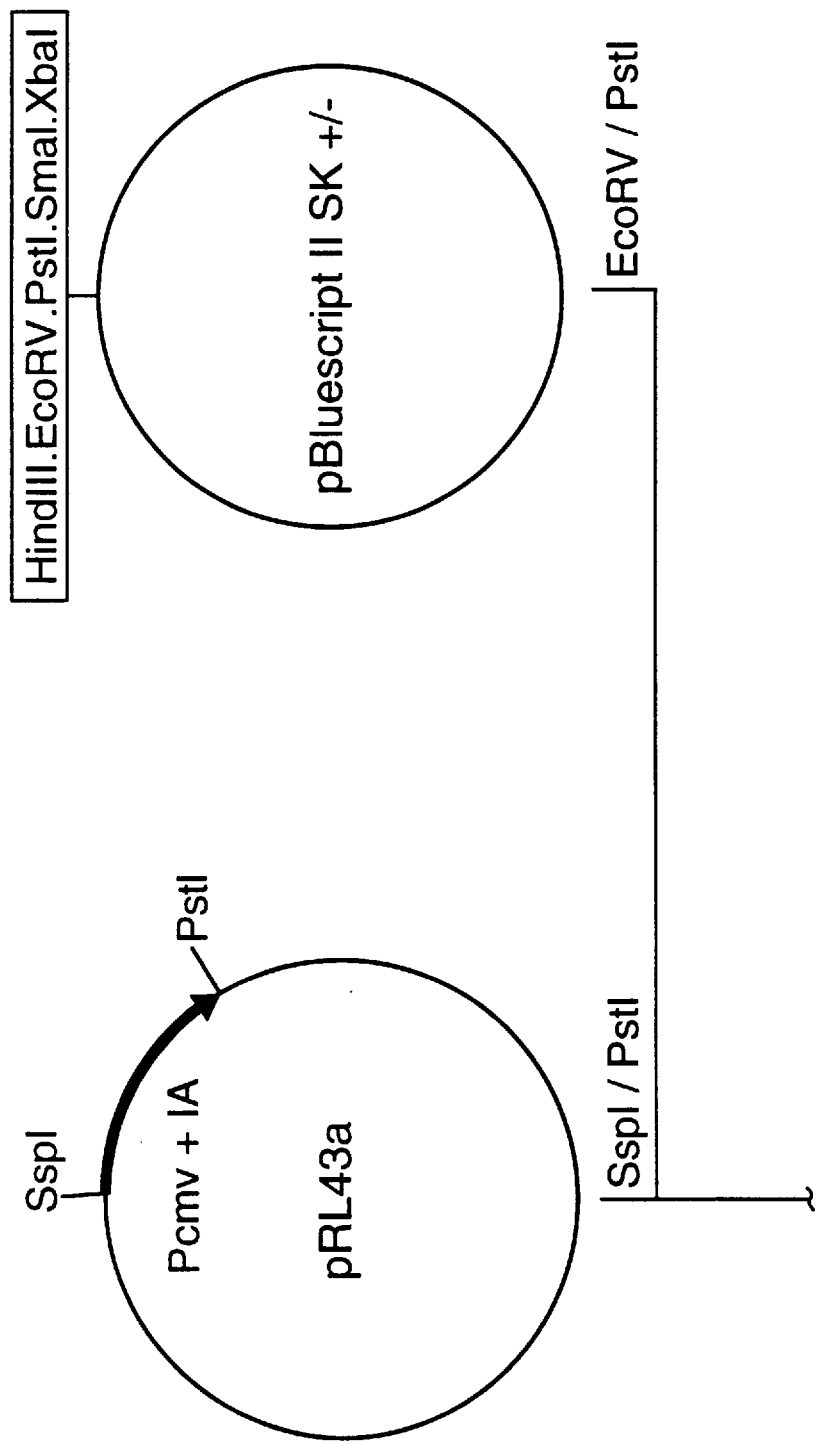
FIGS. 5A–5D show the construction of plasmid pXL2 containing a gene encoding a secreted form of the RSV F protein and containing the rabbit β-globin Intron II sequence.
Figure 5B:
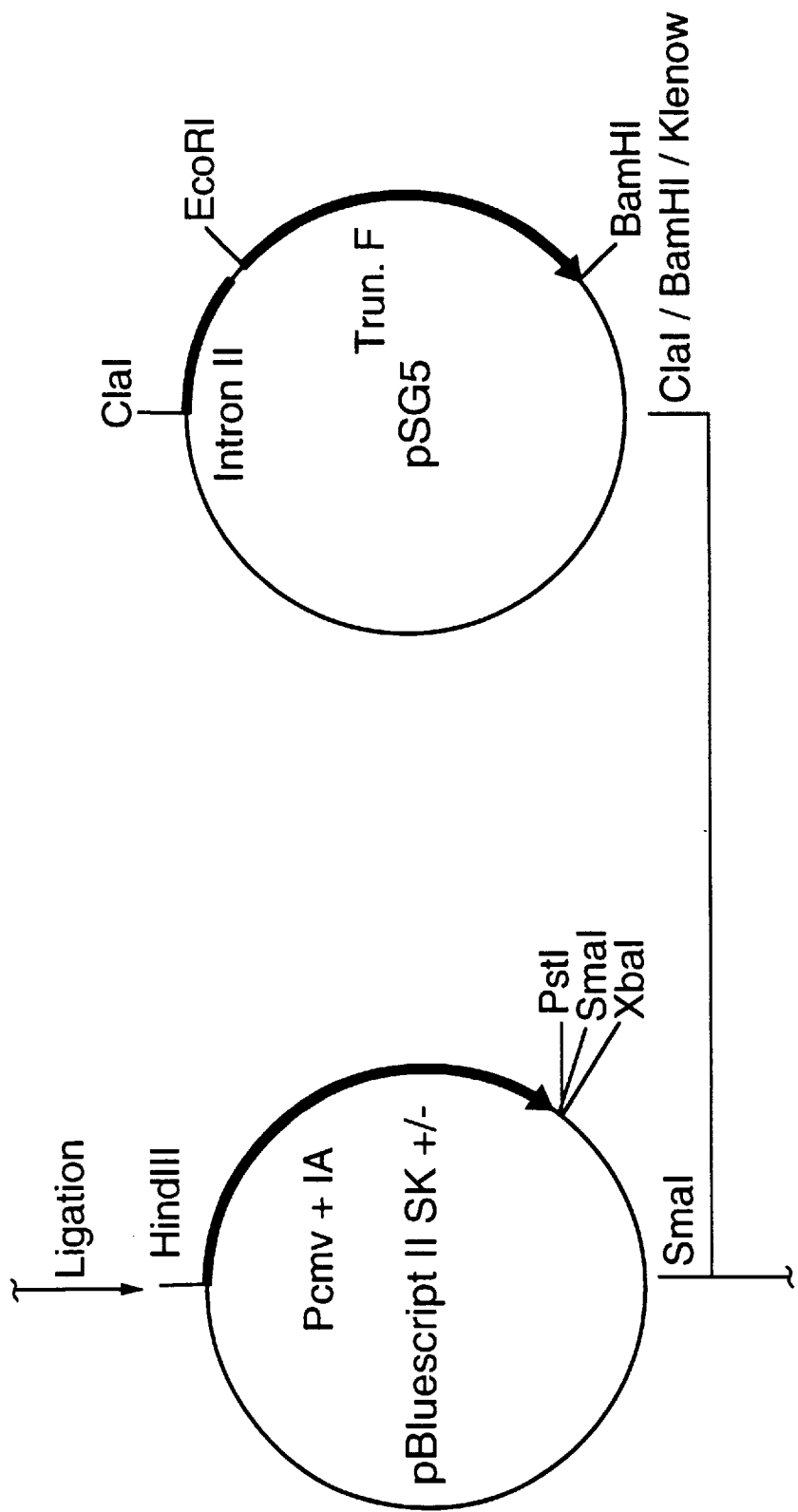
Figure 5C:
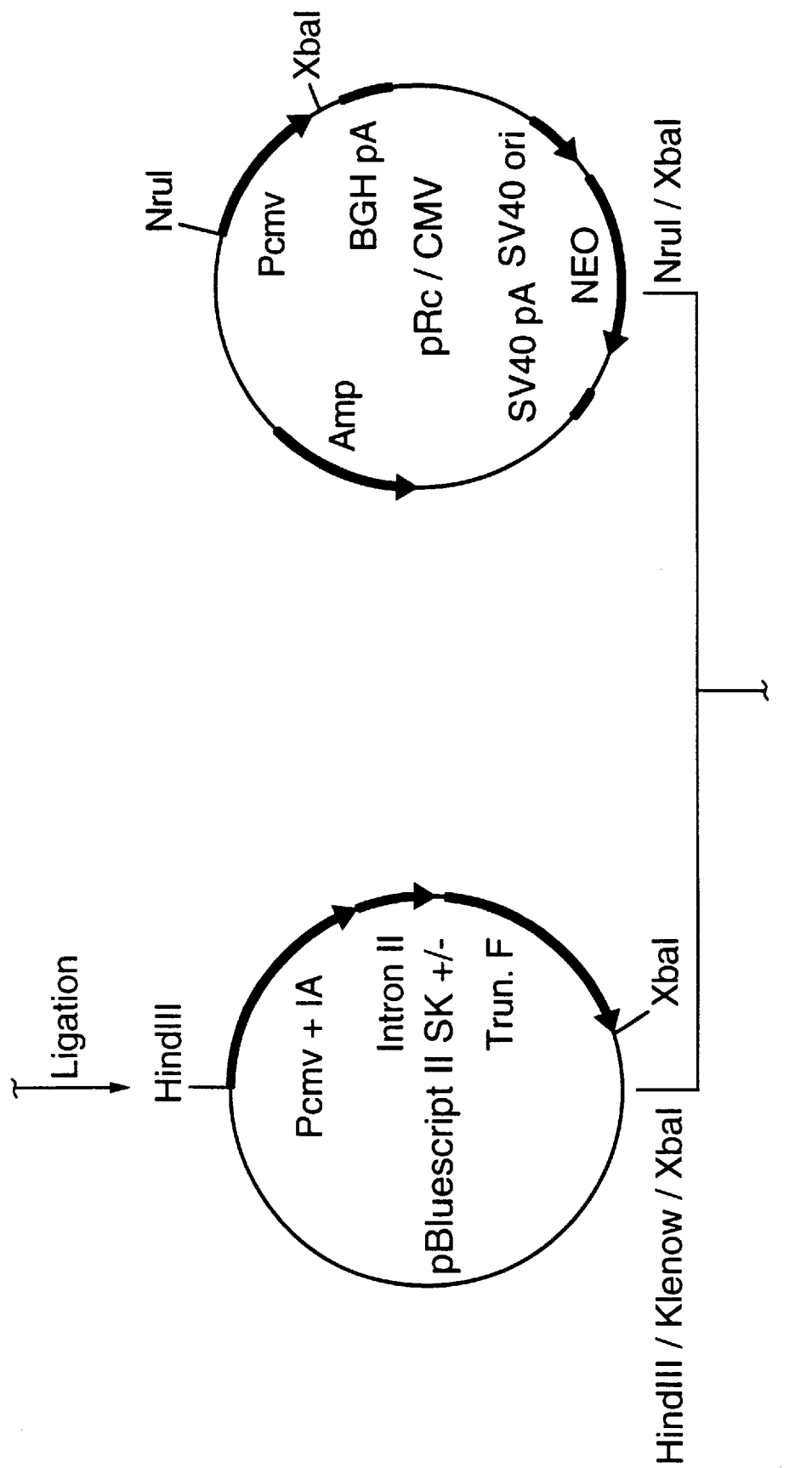
Figure 5D:
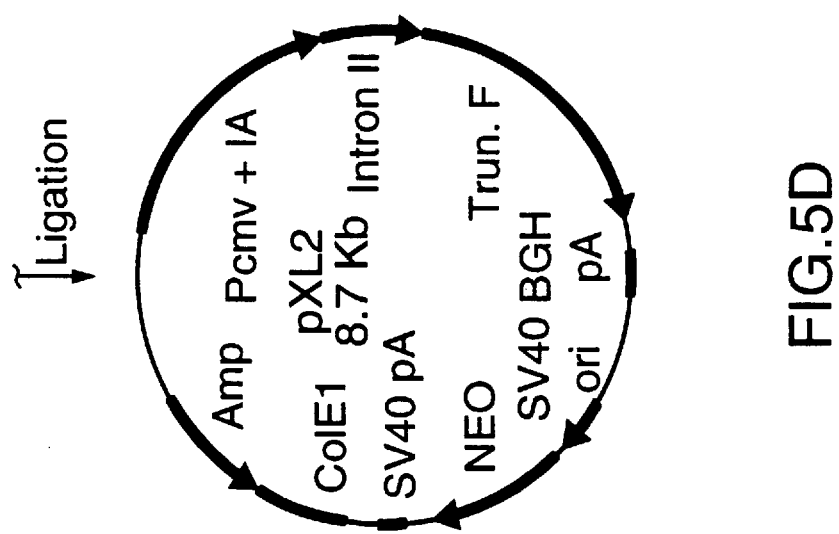
Figure 7A:
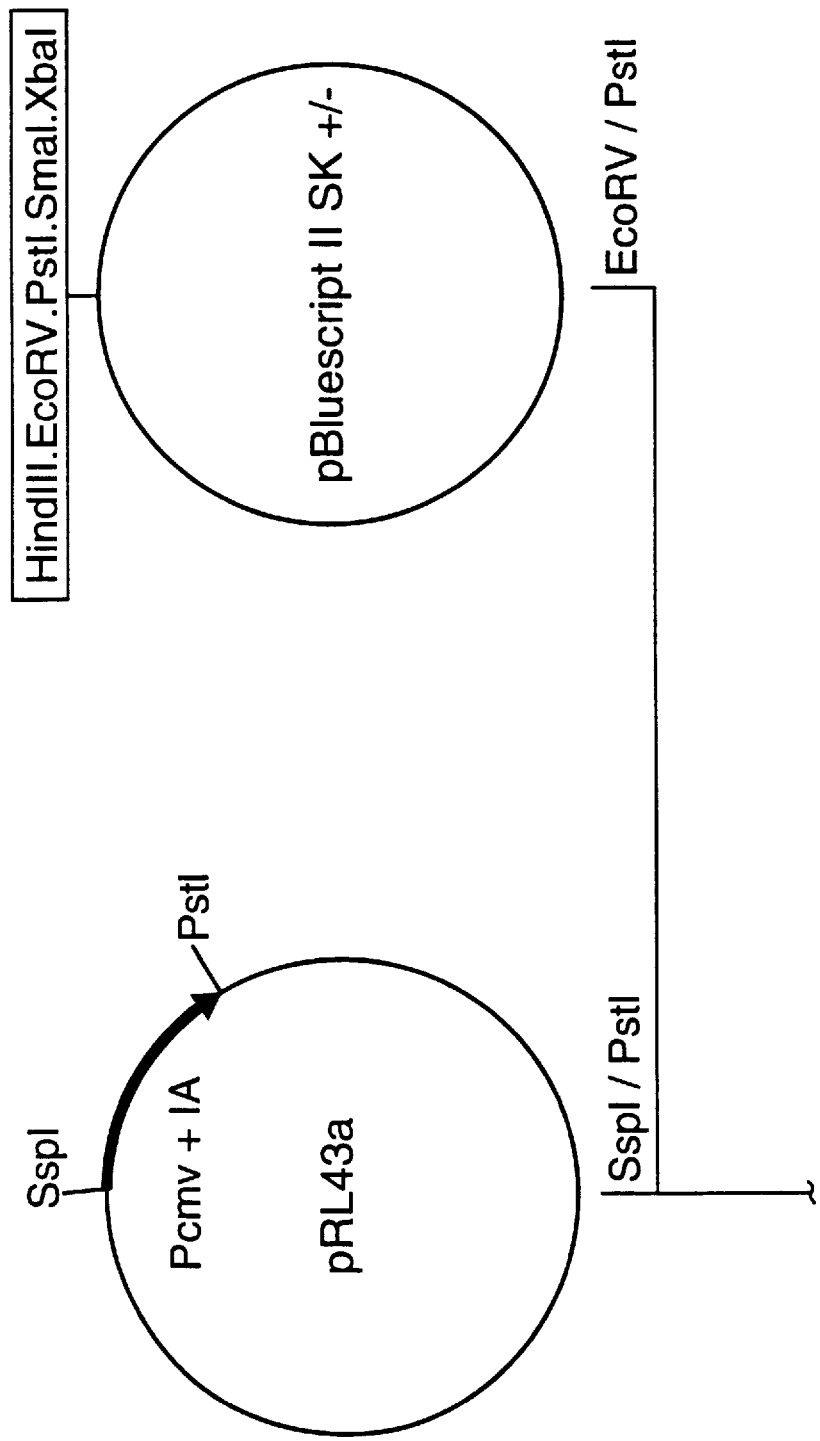
FIGS. 7A–7D show the construction of plasmid pXL4 containing a gene encoding a membrane attached form of the RSV F protein and containing the rabbit β-globin Intron II sequence.
Figure 7B:
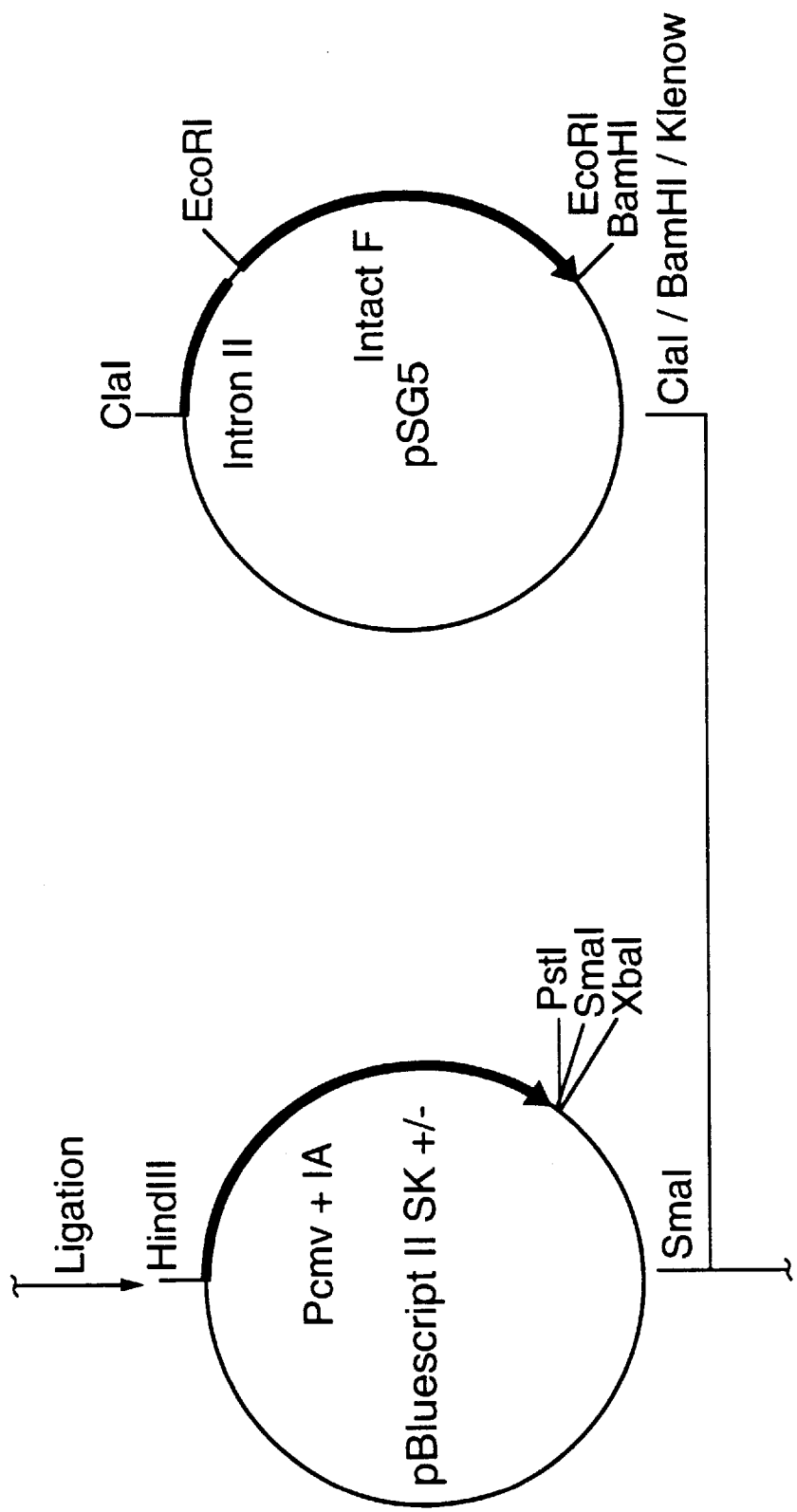
Figure 7C:
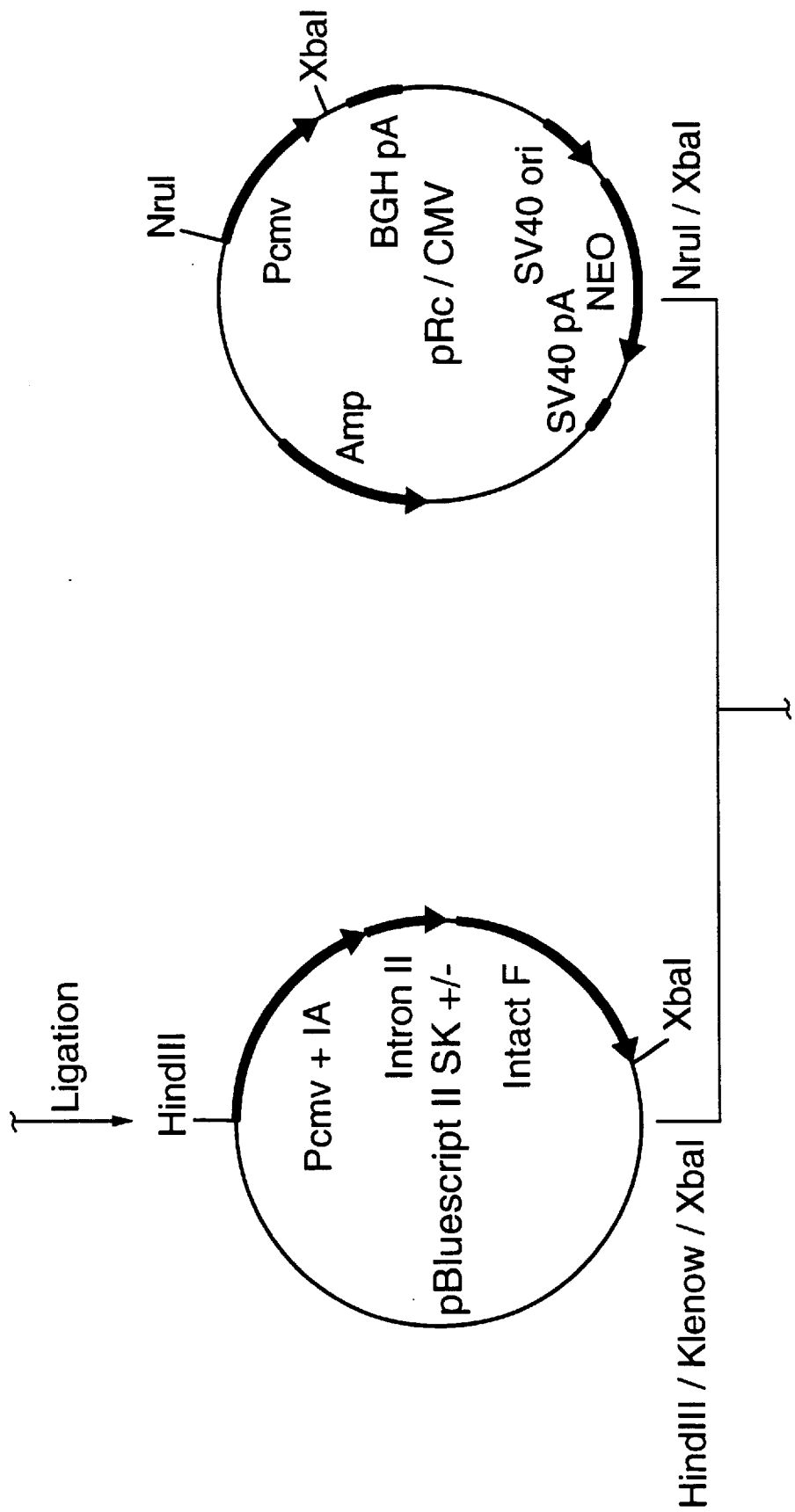
Figure 7D:
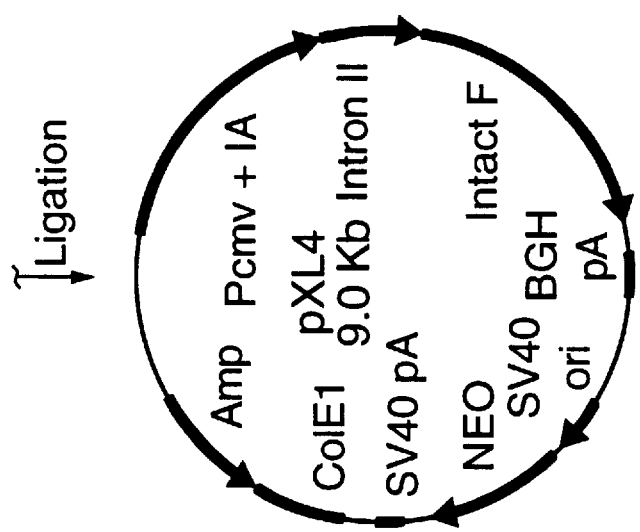

The constructs containing the Intron II sequence, CMV promoter and nucleotide sequence coding for the truncated RSV F protein, i.e. plasmid pXL2 (FIG. 5), induced complete protection in mice against challenge with live RSV, as seen in the Examples below, when the construct was administered in vivo. In addition, the constructs containing the Intron II sequence, CMV promoter and nucleotide sequence coding for the full-length RSV F protein, i.e. plasmid pXL4 (FIG. 7), also conferred protection in mice to challenge with live RSV, as seen from the Examples below.

The vector provided herein may also comprise a third nucleotide sequence encoding a further antigen from RSV, an antigen from at least one other pathogen or at least one immunomodulating agent, such as cytokine. Such vector may contain said third nucleotide sequence in a chimeric or a bicistronic structure. Alternatively, vectors containing the third nucleotide sequence may be separately constructed and coadministered to a host, with the nucleic acid molecule provided herein.

The vector may further comprise a nucleotide sequence encoding a heterologous signal peptide, such as human tissue plasminogen activator (TPA), in place of the endogenous signal peptide.

It is clearly apparent to one skilled in the art, that the various embodiments of the present invention have many applications in the fields of vaccination, diagnosis, treatment of, RSV infections. A further non-limiting discussion of such uses is further presented below.

1. Vaccine Preparation and Use

Immunogenic compositions, suitable to be used as vaccines, may be prepared from the RSV F genes and vectors as disclosed herein. The vaccine elicits an immune response in a subject which includes the production of anti-F antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640, ref. 17) or the nucleic acid may be associated with an adjuvant, as described in more detail below. Liposomes comprising cationic lipids interact spontaneously and rapidly with polyanions such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The RSV F genes and vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate. These compositions can take the form of solutions, suspensions, tablets, pills, capsules, sustained release formulations or powders and contain about 1 to 95% of the RSV F genes and vectors.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the RSV F protein and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 µg to about 1 mg of the RSV F genes and vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the vector comprising a first nucleotide sequence encoding an F protein of RSV may be delivered in conjunction with a targeting molecule to target the vector to selected cells including cells of the immune system.

The polynucleotide may be delivered to the host by a variety of procedures, for example, Tang et al. (ref. 10) disclosed that introduction of gold microprojectiles coated with DNA encoding bovine growth hormone (BGH) into the skin of mice resulted in production of anti-BGH antibodies in the mice, while Furth et al. (ref. 11) showed that a jet injector could be used to transfect skin, muscle, fat and mammary tissues of living animals.

2. Immunoassays

The RSV F genes and vectors of the present invention are useful as immunogens for the generation of anti-F antibodies for use in immunoassays, including enzyme-linked immunosorbent assays (ELISA), RIAs and other non-enzyme linked antibody binding assays or procedures known in the art. In ELISA assays, the vector first is administered to a host to generate antibodies specific to the RSV F protein. These RSV F-specific antibodies are immobilized onto a selected surface, for example, a surface capable of binding the antibodies, such as the wells of a polystyrene microtiter plate. After washing to remove incompletely adsorbed antibodies, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound RSV F specific antibodies, and subsequent washing, the occurrence, and even amount, of immunocomplex formation may be determined.

BIOLOGICAL MATERIALS

Certain plasmids that contain the gene encoding RSV F protein and referred to herein have been deposited with the America Type Culture Collection (ATCC) located at 10801 University Boulevard, Manassas, Va. 20110-2209, U.S.A., pursuant to the Budapest Treaty and prior to the filing of this application.

Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
|---------|------------------|----------------|
| pXL1    | 97167            | May 30, 1995   |
| pXL2    | 97168            | May 30, 1995   |

-continued

| Plasmid | ATCC Designation | Date Deposited |
|---------|------------------|----------------|
| pXL3    | 97169            | May 30, 1995   |
| pXL4    | 97170            | May 30, 1995   |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the construction of vectors containing the RSV F gene.

FIG. 1 shows a restriction map of the gene encoding the F protein of Respiratory Syncytial Virus and FIG. 2 shows the nucleotide sequence of the gene encoding the full-length RSV F protein (SEQ ID No: 1) and the deduced amino acid sequence (SEQ ID No: 2). FIG. 3 shows the gene encoding the secreted RSV F protein (SEQ ID No: 3) and the deduced amino acid sequence (SEQ ID No: 4).

Figure 6A:
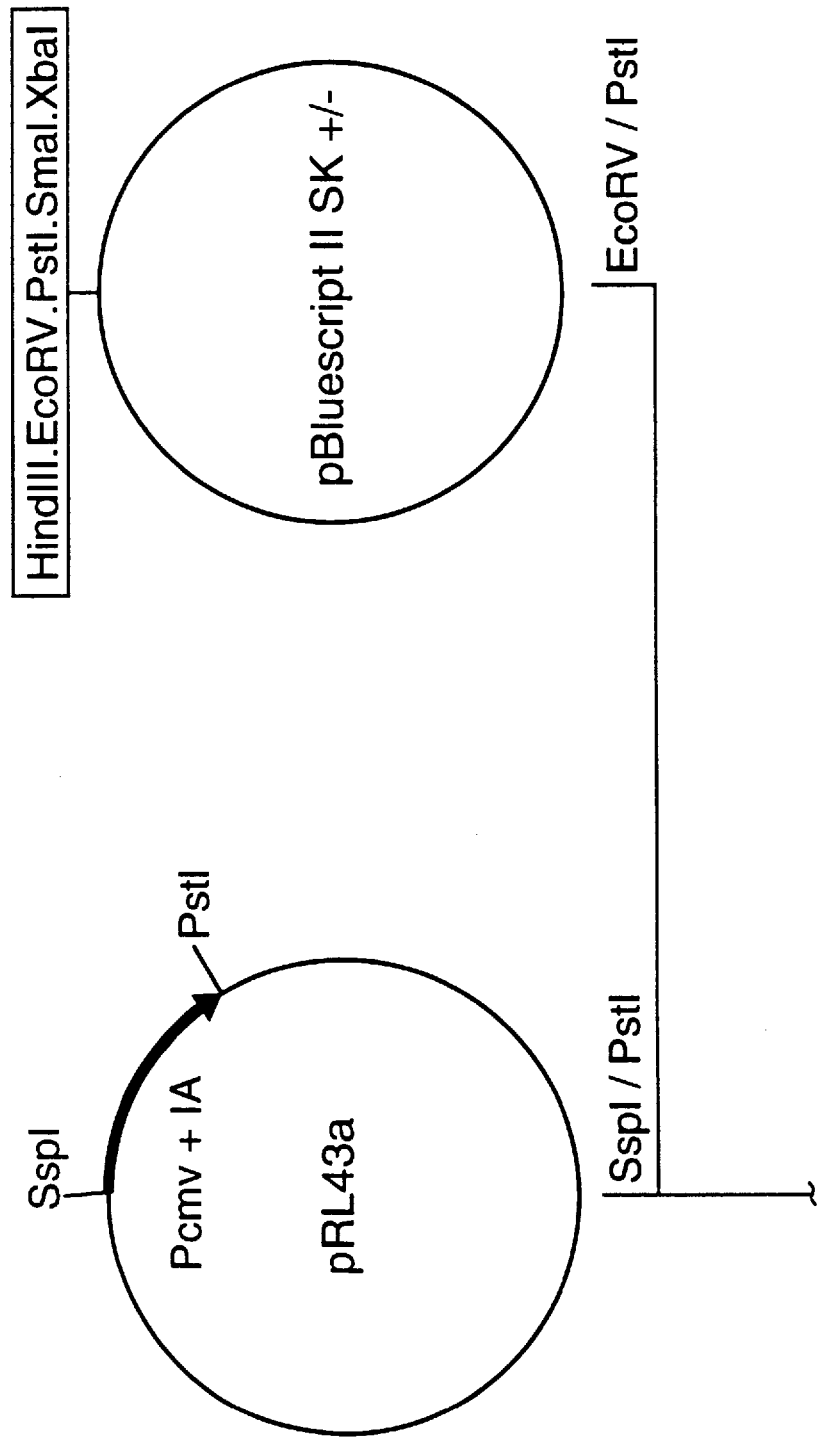
FIGS. 6A–6D show the construction of plasmid pXL3 containing the gene encoding a membrane attached form of the RSV F protein.
Figure 6B:
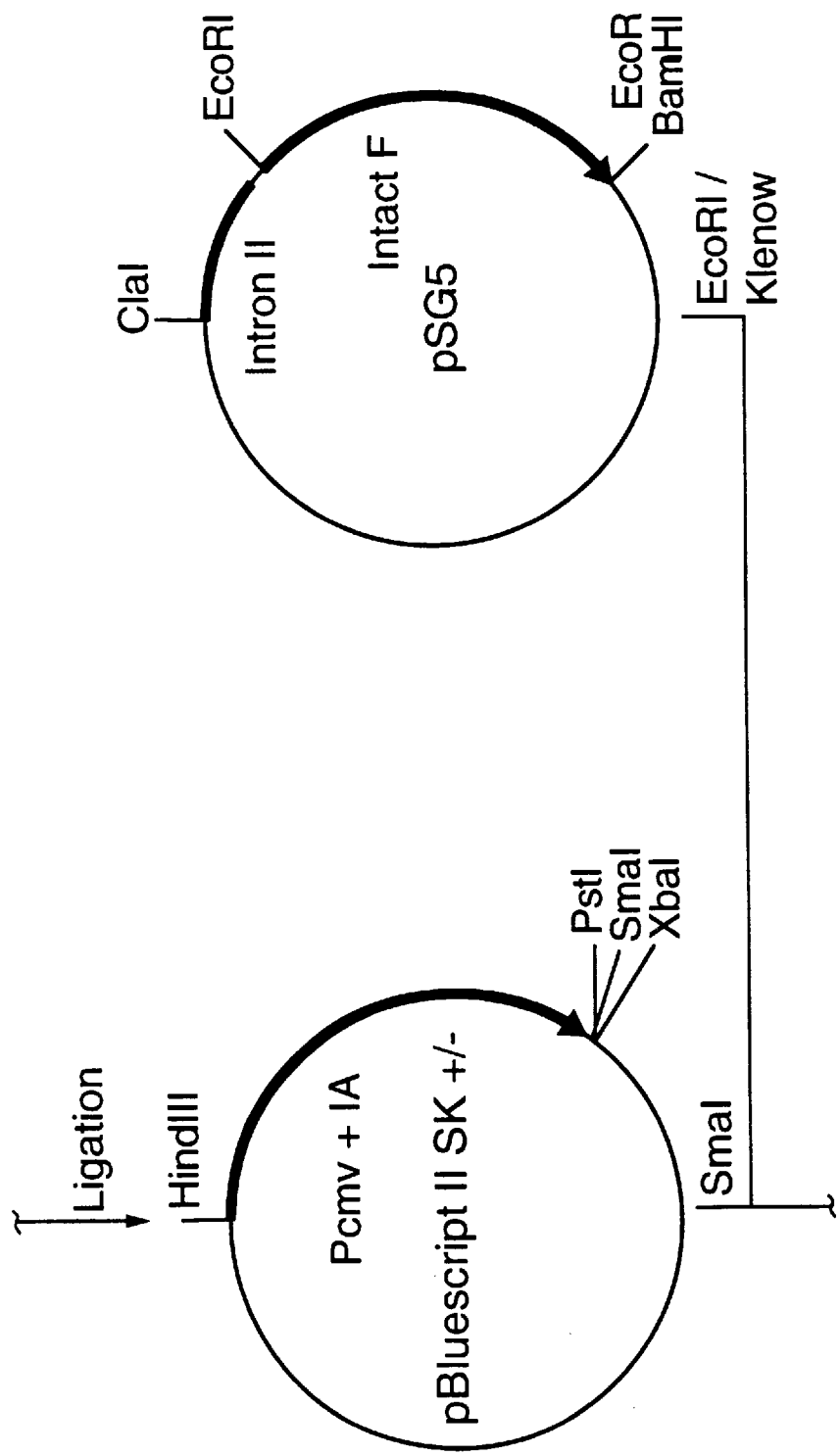
Figure 6C:
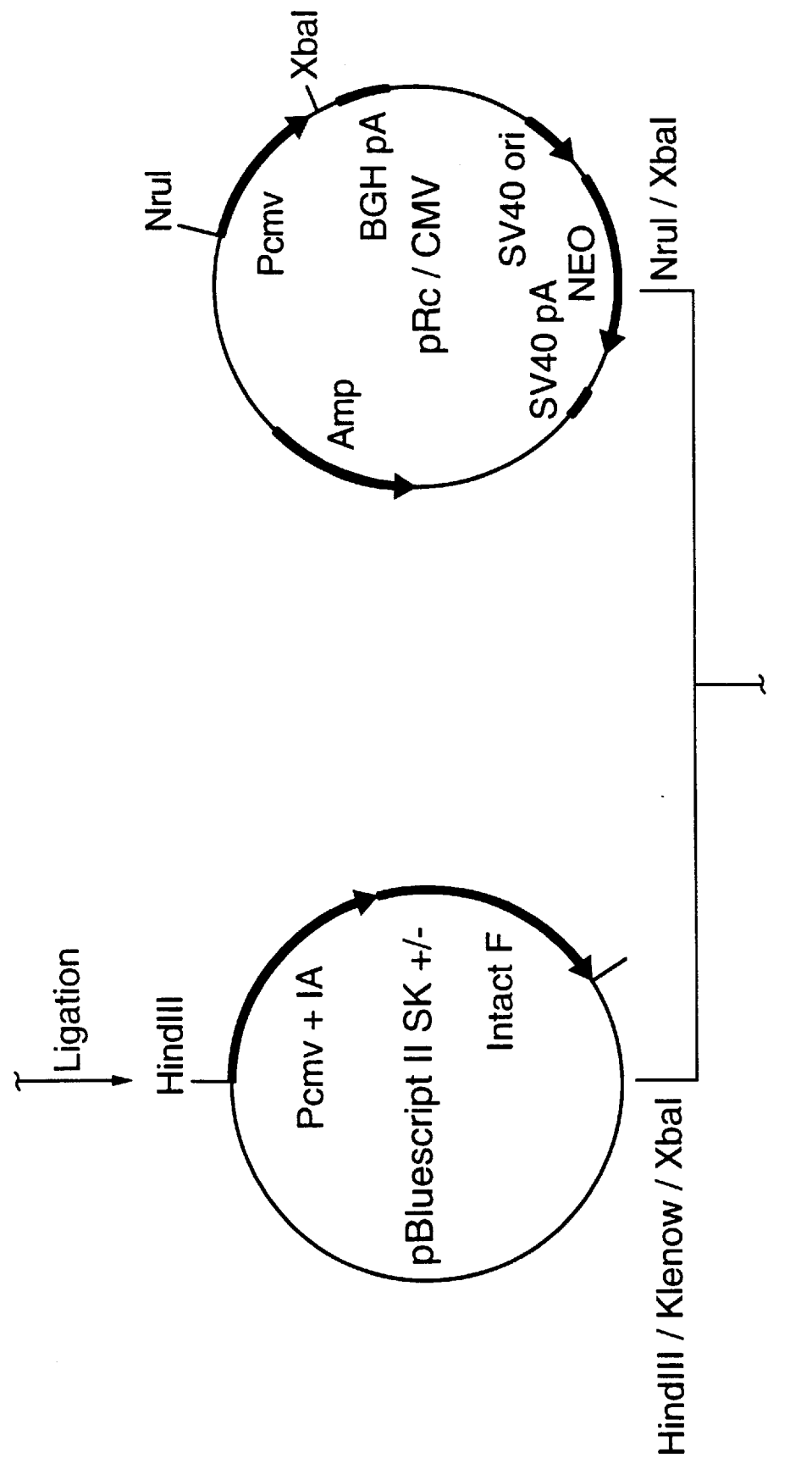
Figure 6D:
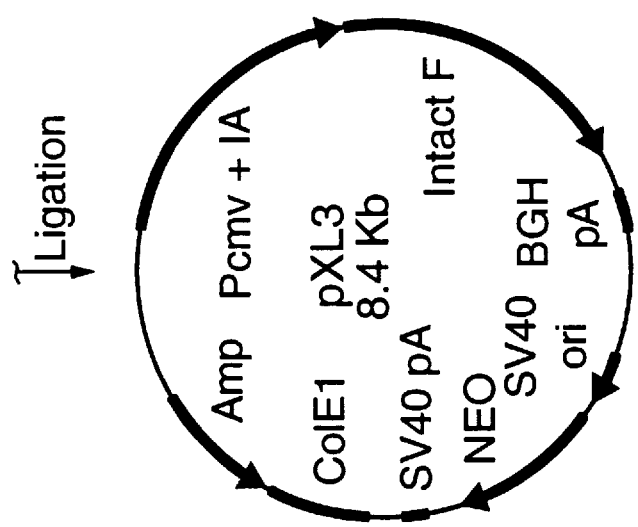

A set of four plasmid DNA constructs were made (as shown schematically in FIGS. 4 to 7) in which cDNA encoding the RSV-F was subcloned downstream of the immediate-early promoter, enhancer and intron A sequences of human cytomegalovirus (CMV) and upstream of the bovine growth hormone (BGH) poly-A site. The 1.6 Kb Sspl-PstI fragment containing the promoter, enhancer and intron A sequences of CMV Towne strain were initially derived from plasmid pRL43a obtained from Dr. G. S. Hayward of Johns Hopkins University (Pizzorno et al., J. Virol. 62, 1167–1179, 1988) and subcloned between EcoRV and Pstl sites of pBluescript 11 SK +/− (Stratagene). For the construction of plasmids expressing the secretory form of the F protein (PXLI and pXL2 in FIGS. 4 and 5), the 1.6 Kb EcoRl-BamHI fragment containing the truncated form of the F cDNA originally cloned from a clinical isolate belonging to subgroup A was excised from PRSVF (ref. 18 and WO 93/14207) and subcloned between EcoRl and BamHl sites of pSG5 (Strategene, ref. 14). Either the 1.6 Kb EcoRl-BamHl fragment or the 2.2 Kb ClaI-BamHI fragment was then excised from the pSG5 construct, filled-in with Klenow and subcloned at the SmaI site of the pBluescript II SK +/− construct containing the promoter and intron A sequences. The 0.6 Kb ClaI-EcoRI fragment derived from pSG5 contained the intron II sequences from rabbit β-globin. Subsequently, the plasmids were digested with HindIII, filled-in with Klenow, and digested with XbaI to yield either a 3.2 or a 3.8 Kb fragment. These fragments were used to replaced the 0.8 Kb NruI-XbaI fragment containing the CMV promoter in pRc/CMV (Invitrogen), resulting in the final pXL1 and pXL2 constructs, respectively.

For the construction of plasmids expressing the full-length F protein (pXL3 and pXL4—FIGS. 6 and 7), the full length RSV F cDNA was excised as a 1.9 Kb EcoRl fragment from a recombinant pBluescript M13-SK (Stratagene) containing the insert (ref. 18 and WO 93/14207) and subcloned at the EcoRl site of pSG5 (Stratagene). Either the 1.9 Kb EcoRI fragment or the 2.5 Kb ClaI-BamHI fragment was then excised from the pSG5 construct, filled-in with Klenow and subcloned at the SmaI site of the pBluescript II SK +/− construct containing the promoter and intron A sequences. The rest of the construction for pXL3 and pXL4 was identical to that for pXL1 and pXL2, as described above. Therefore, except for the CMV promoter and intron A sequences, the rest of the vector components in pXL1–4 were derived from plasmid pRc/CMV. Plasmids pXL1 and pXL2 were made to express a truncated/secretory form of the F protein which carried stop codons resulting in a C-terminal deletion of 48 amino acids including the transmembrane (TM) and the C-terminal cytosolic tail as compared to the intact molecule. In contrast, pXL3 and pXL4 were made to express the intact membrane-attached form of the RSV F molecule containing the TM and the cytosolic C-terminal tail. The rationale for the presence of the intron II sequences in pXL2 and pXL4 was that this intron was reported to mediate the correct splicing of RNAS. Since mRNA for the RSV-F has been suspected to have a tendency towards aberrant splicing, the presence of the intron II sequences might help to overcome this. All four plasmid constructs were confirmed by DNA sequencing analysis.

Plasmid DNA was purified using plasmid mega kits from Qiagen (Chatsworth, Calif., USA) according to the manufacturer's instructions.

Example 2

This Example describes the immunization of mice. Mice are susceptible to infection by RSV as described in ref. 16.

Tibialis anterior muscles of groups of 9 BalB/c mice (male, 6–8 week old) (Jackson Lab.) were injected bilaterally with 2×50 $\mu$g (1 $\mu$g/$\mu$l in PBS) of the four plasmid constructs, respectively. Five days prior to the DNA injection, these muscles were treated bilaterally with cardiotoxin (2×50 $\mu$l of 10 $\mu$M in PBS, Latoxan, France). Pretreatment of the muscles with cardiotoxin has been reported to increase DNA uptake and to enhance the subsequent immune responses by the intramuscular route. These animals were boosted similarly a month later. The group of control mice was immunized with placebo according to the same schedule.

Sera were obtained periodically from immunized mice and analyzed for anti-RSV F-specific antibody titres by ELISA and for RSV-specific plaque-reduction titres in vitro. For the ELISA, 96-well plates were coated with purified RSV F protein at 50 ng/ml to which 2-fold serially diluted serum samples were applied. A goat-anti mouse antibody alkaline phosphatase conjugate was used. The assessment of the plaque reduction titres was essentially accordingly to the method of Prince et al. (ref. 19) using vaccine quantity Vero cells. Four-fold serially diluted sera were incubated with 50 plaque forming units (pfu) of RSV, subtype A2 (Long strain), in culture medium at 37° C. for 1 hr in the presence of 5% $CO_2$. Vero cells were then infected with the mixture. Plaques were fixed and developed 5 days later using mouse anti-RSV-F monoclonal antibodies and donkey anti-mouse antibodies conjugated to alkaline phosphatase. The RSV-specific plaque reduction titre was defined as the dilution of the serum sample yielding 60% reduction in the number of the plaques. This was derived by linear regression from correlating numbers of the remaining plaques with folds of the serial dilutions.

Seventy-five days after the boost immunization, mice were challenged intranasally with $10^{5.4}$ pfu (per animal) of mouse-adapted RSV, A2 subtype. Lungs were asceptically removed 4 days later, weighed and homogenized in 2 mL of complete culture medium. The number of pfu in the lung homogenate was determined as described by Prince et al (ref. 19) using Vero cells.

encoding F protein of RSV can protect against disease caused by this virus.

SUMMARY OF THE DISCLOSURE

In summary of this disclosure, the present invention provides certain novel vectors containing genes encoding an RSV F proteins, methods of immunization using such vectors and methods of diagnosis using such vectors. Modifications are possible within the scope of this invention.

TABLE 1

Protection of Mice Against RSV by Immunization with Genes Encoding the F Protein

| Immunogen | No. Mice | Anti-F Protein ELISA Titre ($Log_2 \pm SD$)* | Mean Plaque Reduction Titre* ($Log_4 \pm SD$) | Mean Virus Lung Titre@ (pfu/g lung) ($Log_{10} \pm SD$) | No. Fully Protected Mice** |
|---|---|---|---|---|---|
| pXL1 | 8 | 9.64 ± 1.85 | 3.74 ± 0.98 | 0.72 ± 0.99 | 5 |
| pXL2 | 9 | 12.42 ± 1.72 | 4.82 ± 0.51 | 0.00 ± 0.00 | 9 |
| pXL3 | 8 | 10.39 ± 2.05 | 4.59 ± 1.16 | 2.77 ± 0.72 | 0 |
| pXL4 | 9 | 12.08 ± 1.13 | 5.18 ± 0.43 | 0.66 ± 1.00 | 6 |
| Placebo*** | 12 | 6.12 ± 2.89 | 0.18 ± 0.62 | 3.92 ± 0.27 | 0 |

*Sera obtained 1 week prior to the viral challenge.
@Detection sensitivity of the assay was $10^{1.96}$ pfu/g lung.
**The term, fully protected mice, refers to animals with undetectable RSV titres in lungs (ref. 17)
***RSV F deficient pXL1

The results of the immunizations are shown in Table 1 below, and were analyzed using SigmaStat Software (Jandel Scientific Software).

Sera obtained from mice immunized with either construct pXL1, pXL2, pXL3 or pXL4 demonstrated significant anti-RSV F ELISA titres as compared to the placebo group (P<0.00061, Mann-Whitney Test). However, there is no significant difference among mice immunized with any of the constructs.

Sera obtained from mice immunized with constructs pXL1, pXL2, pXL3 or pXL4 demonstrated significant plaque reduction titres whereas sera obtained from the placebo group did not (P<0.0001, Mann-Whitney Test). However, there is no significant difference among mice immunized with any of the constructs.

The viral lung titres, four days after viral challenge, are also shown in Table 1. There is a significant difference between mice immunized with either construct pXL1, pXL2, pXL3 or pXL4 and the placebo group (P<0.0001, Mann-Whitney Test). In particular, no virus could be detected in the lungs of mice immunized with vector pXL2. The protection afforded by vector pXL3 was significantly lower than the other vectors.

In terms of the number of mice protected from RSV challenge, there is a significant difference between mice immunized with vectors pXL1, pXL2 and pXL4 and the placebo group or mice immunized with vector pXL3 (P<0.004, Fisher Exact Test). Furthermore, only the pXL2 vector which expresses the secretory form of the RSV F protein and contains the β-globin intron II was able to confer complete protection in all immunized mice. In contrast, the pXL3 vector which expresses the full length F protein and does not contain the intron II failed to induce significant protection. None of the mice in the placebo group were protected from viral challenge.

The data presented in Table 1 clearly demonstrate that immunization of a relevant RSV animal model with genes

REFERENCES

1. McIntosh K., Canock, R. M. In: Fields BN, Knipe, DM, editors. Virology. New York: Raven Press: 1990: 1045–1072.
2. Katz S L., In: New Vaccine Development establishing priorities. Vol. 1. Washington: National Academic Press: 1985: 397–409.
3. Wertz G W, Sullender W M., Biotechnology 1992; 20: 151–176.
4. Johnson et al., J. Virol 1987, 61: 3163–3166.
5. Pemberton et al., J. Gen Virol. 1987, 68: 2177–2182.
6. Crowe, J. E., Vaccine 1995, 13: 415–421.
7. WO 90/11092
8. WO 94/21797
9. Ulmer, Current Opinion, Invest Drugs, 1993, 2: 983–989.
10. Tang et al., Nature 1992, 356: 152–154.
11. Furth et al. Analytical Biochemistry, 1992, 205: 365–368.
12. Pizzorno et al., J. Virol. 1988, 62: 1167–1179.
13. Chapman, B. S.; Thayer, R. M.; Vincent, K. A. and Haigwood, N. L., Nucl. Acids. Res. 1991, 19: 3979–3986.
14. Green, S. Isseman, I., and Sheer, E., Nucl. Acids. Res. 1988, 16: 369.
15. Breathnack, R. and Harris, B. A., Nucl. Acids Res. 1983, 11: 7119–7136.
16. Graham, B. S.; Perkins M. D.; Wright, P. F. and Karzon, D. T. J. Mod. Virol. 1988 26: 153–162.
17. Nabel, G. J. 1993, Proc. Natl. Acad. Sci. USA 90: 11307–11311.
18. Du, R. P et al. 1994., Biotechnology 12: 813–818.
19. Prince, G. A. et al, 1978. Ame. J. Pathol. 93: 771–790.

What we claim is:

1. A method of immunizing a host against disease caused by infection with respiratory syncytial virus (RSV), which comprises administering to said host an effective amount of a plasmid vector comprising a nucleotide sequence encoding an RSV F protein lacking a transmembrane region and a promoter sequence operatively coupled to said nucleotide sequence for expression of said RSV F protein in said host.

2. The method of claim 1 wherein said host is a human.

3. The method of claim 2 wherein said promoter sequence is an immediate early cytomegalovirus promoter.

4. A method of producing a vaccine for protection of a host against disease caused by infection with respiratory syncytial virus (RSV), which comprises:

isolating a nucleotide sequence encoding an RSV F protein from which the transmembrane region is absent, operatively linking said nucleotide sequence to a promoter sequence to produce a plasmid vector, the promoter sequence directing expression of said RSV F protein when introduced to a host to produce an immune response to said RSV F protein, formulating said vector as a vaccine for in vivo administration to a host.

5. A vaccine produced by the method of claim 4.

* * * * *